(12) United States Patent
Beus et al.

(10) Patent No.: US 12,398,832 B2
(45) Date of Patent: Aug. 26, 2025

(54) METHODS OF USING COMPRESSION COLLARS FOR COUPLING A TUBE TO A TUBE FITTING

(71) Applicant: Life Technologies Corporation, Carlsbad, CA (US)

(72) Inventors: Ryan S. Beus, Providence, UT (US); Brandon R. Burtenshaw, Logan, UT (US); Eric Davis, Smithfield, UT (US); Patrick L Draper, Smithfield, UT (US); Michael E. Goodwin, Logan, UT (US); Brandon M. Knudsen, Hyrum, UT (US); Jeremy K. Larsen, Providence, UT (US); Kevin R. Pickup, Paradise, UT (US)

(73) Assignee: Life Technologies Corporation, Carlsbad, CA (US)

( * ) Notice: Subject to any disclaimer, the term of this patent is extended or adjusted under 35 U.S.C. 154(b) by 145 days.

(21) Appl. No.: 18/486,070

(22) Filed: Oct. 12, 2023

(65) Prior Publication Data
US 2024/0035601 A1 Feb. 1, 2024

Related U.S. Application Data

(60) Continuation of application No. 17/576,671, filed on Jan. 14, 2022, now Pat. No. 11,821,553, which is a
(Continued)

(51) Int. Cl.
*B32B 41/00* (2006.01)
*A61M 39/12* (2006.01)
(Continued)

(52) U.S. Cl.
CPC ............ *F16L 33/207* (2013.01); *A61M 39/12* (2013.01); *B29C 65/565* (2013.01); *B29C 65/68* (2013.01);
(Continued)

(58) Field of Classification Search
CPC ...... F16L 33/207; F16L 33/227; A61M 39/12; B29C 65/565; B29C 65/68;
(Continued)

(56) References Cited

U.S. PATENT DOCUMENTS 2,423,632 A 7/1947 Ansorge
2,433,602 A 12/1947 Coss
(Continued)

FOREIGN PATENT DOCUMENTS

AT 377346 B 3/1985
CN 102472426 A 5/2012
(Continued)

OTHER PUBLICATIONS

International Search Report and Written Opinion dated Apr. 9, 2018, issued in PCT Application No. PCT/US2018/012518, filed Jan. 4, 2018.
(Continued)

*Primary Examiner* — Michael N Orlando
*Assistant Examiner* — Joshel Rivera

(57) ABSTRACT

A method for coupling a tube to a tube fitting includes radially outwardly expanding a tubular compression collar from a constricted state to an expanded state, the compression collar having a throughway extending there through and being made of a resiliently flexible material. An end of the tube is inserted within the throughway of the expanded compression collar, the tube bounding a passage. A tube fitting is inserted within the passage of the tube. The compression collar is allowed to resiliently rebound back towards the constricted state so that the compression collar pushes the tube against the tube fitting.

21 Claims, 27 Drawing Sheets

Related U.S. Application Data division of application No. 15/863,031, filed on Jan. 5, 2018, now Pat. No. 11,371,634.

(60) Provisional application No. 62/442,889, filed on Jan. 5, 2017.

(51) Int. Cl.
| | |
|---|---|
| *B29C 65/00* | (2006.01) |
| *B29C 65/56* | (2006.01) |
| *B29C 65/68* | (2006.01) |
| *F16L 33/207* | (2006.01) |
| *F16L 33/22* | (2006.01) |
| *B29L 31/24* | (2006.01) |

(52) U.S. Cl.
CPC .......... *B29C 66/1122* (2013.01); *B29C 66/12* (2013.01); *B29C 66/1222* (2013.01); *B29C 66/1224* (2013.01); *B29C 66/131* (2013.01); *B29C 66/30321* (2013.01); *B29C 66/5344* (2013.01); *B29C 66/7315* (2013.01); *B29C 66/73753* (2013.01); *B29C 66/7392* (2013.01); *B29C 66/7394* (2013.01); *F16L 33/227* (2013.01); *B29C 66/71* (2013.01); *B29L 2031/24* (2013.01)

(58) Field of Classification Search
CPC . B29C 66/1122; B29C 66/12; B29C 66/1222; B29C 66/1224; B29C 66/131; B29C 66/30321; B29C 66/5344; B29C 66/7315; B29C 66/73753; B29C 66/7392; B29C 66/7394; B29C 66/71; B29L 2031/24; B29K 2023/06; B29K 2023/065
USPC .................. 156/60, 64, 350, 351, 378, 379
See application file for complete search history.

(56) References Cited

U.S. PATENT DOCUMENTS

| | | |
|---|---|---|
| 3,589,752 A | 6/1971 | Spencer et al. |
| 4,111,469 A | 9/1978 | Kavick |
| 4,278,279 A | 7/1981 | Zimmerman |
| 4,537,183 A | 8/1985 | Fogarty |
| 4,577,894 A | 3/1986 | Wake |
| 5,284,368 A | 2/1994 | Oetiker et al. |
| 5,340,167 A | 8/1994 | Morse |
| D383,053 S | 9/1997 | Schrader et al. |
| 5,700,528 A | 12/1997 | Fitch |
| 5,882,047 A | 3/1999 | Ostrander et al. |
| 6,170,885 B1 | 1/2001 | Stuemky |
| 6,231,085 B1 | 5/2001 | Olson |
| 6,270,125 B1 | 8/2001 | Rowley et al. |
| D568,969 S | 5/2008 | Bucchi |
| 7,464,969 B2 | 12/2008 | Poll |
| D612,020 S | 3/2010 | Ward |
| 8,146,225 B2 | 4/2012 | Olinger et al. |
| 8,365,382 B2 | 2/2013 | Hedstrom |
| D691,246 S | 10/2013 | Ward |
| D706,126 S | 6/2014 | Orow |
| D793,216 S | 8/2017 | Divers et al. |
| D803,994 S | 11/2017 | Sekine |
| D850,248 S | 6/2019 | Byerly et al. |
| D886,994 S | 6/2020 | Lundkvist et al. |
| D919,775 S | 5/2021 | Kluss et al. |
| 11,371,634 B2 | 6/2022 | Beus et al. |
| 11,821,554 B2 | 11/2023 | Beus et al. |
| D1,013,126 S | 1/2024 | Hendricks |
| D1,028,296 S | 5/2024 | Sanson |
| 2008/0136180 A1* | 6/2008 | Dittmar ................. F16L 13/004 285/381.2 |
| 2008/0315579 A1 | 12/2008 | Smahl et al. |
| 2009/0152864 A1 | 6/2009 | Olinger et al. |
| 2009/0302602 A1 | 12/2009 | Larsson |
| 2010/0308503 A1 | 12/2010 | Schramm et al. |
| 2013/0140739 A1 | 6/2013 | Lundequist et al. |
| 2013/0307260 A1 | 11/2013 | Laakso et al. |
| 2015/0091299 A1 | 4/2015 | Kauppi |
| 2015/0219086 A1 | 8/2015 | Puff et al. |
| 2016/0305582 A1 | 10/2016 | Blomberg |
| 2017/0069735 A1 | 3/2017 | Oh et al. |
| 2018/0065282 A1 | 3/2018 | Runyan |
| 2018/0066776 A1 | 3/2018 | Roper |
| 2018/0066784 A1 | 3/2018 | Runyan |
| 2018/0198000 A1 | 7/2018 | Romanescu et al. |
| 2022/0136632 A1 | 5/2022 | Beus et al. |
| 2022/0168932 A1 | 6/2022 | Runyan |
| 2022/0228686 A1 | 7/2022 | Beus et al. |

FOREIGN PATENT DOCUMENTS

| | | |
|---|---|---|
| CN | 103791019 A | 5/2014 |
| CN | 203609751 U | 5/2014 |
| CN | 104810390 A | 7/2015 |
| CN | 105813672 A | 7/2016 |
| CN | 208587625 U | 3/2019 |
| DE | 19545361 A1 | 6/1997 |
| EP | 1 741 968 A1 | 1/2007 |
| EP | 1907748 A1 | 4/2008 |
| EP | 2064049 A2 | 6/2009 |
| EP | 2 064 049 B1 | 3/2010 |
| EP | 2170583 A1 | 4/2010 |
| EP | 2 481 966 A1 | 8/2012 |
| EP | 2 170 583 B1 | 9/2013 |
| EP | 1 907 748 B1 | 3/2014 |
| EP | 2 775 190 A1 | 9/2014 |
| TW | 201511234 A | 3/2015 |
| WO | WO-95/19867 A1 | 7/1995 |
| WO | WO-01/73330 A2 | 10/2001 |
| WO | WO-2007/006863 A1 | 1/2007 |
| WO | WO-2008/023351 A2 | 2/2008 |
| WO | WO-2009/004407 A1 | 1/2009 |
| WO | WO-2012/104291 A1 | 8/2012 |
| WO | WO-2012/123501 A1 | 9/2012 |
| WO | WO-2014/181789 A1 | 11/2014 |
| WO | WO-2015191991 A1 | 12/2015 |
| WO | WO-2016/021300 A1 | 2/2016 |
| WO | WO-2016/210300 A1 | 12/2016 |

OTHER PUBLICATIONS

European Examination Report for European Application No. EP18701846.0, mailed on Dec. 23, 2021,3 pages.

* cited by examiner

METHODS OF USING COMPRESSION COLLARS FOR COUPLING A TUBE TO A TUBE FITTING

CROSS-REFERENCE TO RELATED APPLICATIONS

This application is a continuation application of U.S. Divisional application Ser. No. 17/576,671, filed on Jan. 14, 2022, which is divisional of U.S. application Ser. No. 15/863,031, filed Jan. 5, 2018, now U.S. Pat. No. 11,371,634, issued on Jun. 28, 2022, which claims the benefit of U.S. Provisional Application No. 62/442,889, filed Jan. 5, 2017, which are incorporated herein by specific reference.

BACKGROUND OF THE INVENTION

1. The Field of the Invention

The present invention relates to compression collars used for securing tubes to tube fittings and methods of use.

2. The Relevant Technology

Within the biopharmaceutical industry there exists many applications where various fluids are stored, mixed, processed, and transported to and from biological processing containers. Such fluids can be very expensive and it is typically critical that they be maintained in a sterile environment. To help maintain sterility and to eliminate the need for cleaning, most fluids are processed and stored in sterile polymeric bags. To facilitate transfer of fluid between different bags, polymeric tubing is connected to barbed ports secured to the bags.

One weakness with the traditional friction fit connection between the tubing and the barbed port is that when the fluid system is pressurized, the applied pressure can cause the tubing to separate or lift off of the face of the barb on the port. This separation can cause potential leaks and contamination of the fluid. Another problem exists when customers handle the fluid system and manipulate the barbed port connection. Such handling can again cause the sealed connection between the barbed port and the tubing to be broken, thereby risking contamination of the fluid.

To assist in eliminating the above problems, the biopharmaceutical industry has adopted the use of cable ties, also known as zip ties, which are manually secured around the tubing over each barbed port. The cable ties provide a compressive force on the tubing that produces a sealed engagement between the tubing and the port, even when the system is handled or pressurized. For example, a common cable tie is normally made of nylon and includes a locking head having an opening extending therethrough and an elongated, flexible tape section that projects from the locking head. Teeth are formed on the tape section. A pawl projects into the opening of the locking head and is configured to engage the teeth to form a ratchet. During use, the free end of the tape section is passed around a tube and pulled through the opening of the locking head to form a continuous loop. As the tape section is pulled further through the opening, the continuous loop constricts to produce a compressive force on the tube that the cable tie encircles. Concurrently, the pawl engages with the teeth so that the tape section can be freely pulled into the opening of the locking head but is prevented from being pulled out of the opening of the locking head, thereby holding the cable tie in the constricted state.

Although cable ties have been largely found to be effective, such use has its shortcomings. For example, once a cable tie is secured in place, the unused free end of the tape section is typically cut off. As a result of the cut, however, the remaining tape section now has sharp corners that can potentially puncture or otherwise damage the polymeric bags of the fluid system, especially when the polymeric bags are folded over the cable ties for transport or storage. Although bubble wrap or other packing can be placed over each cable tie, such a process is time consuming, labor intensive and subject to error or failure.

Furthermore, a cable tie does not provide a uniform compressive force around the tube to which it is secured. Rather, as a result of the geometry of the cable tie, there is a location at the intersection of where the tape section feeds into the locking head where a gap or at least decreased compressive force is typically formed between the cable tie and tubing. As a result, there is an area of weakness between the tube and barbed port that has a higher probability of leaking and permitting contamination of the fluid. Cable ties are also problematic in that they can be difficult to attach and difficult to control the amount of compressive force they apply. In part, this is because cable ties are narrow and thus only cover a small portion of the port. In addition, cable ties are tightened by a hand tool that can result in variance in tension between different cable ties. Furthermore, after a cable tie is tensioned, it will naturally relax over time, thereby decreasing compression on the port. Other problems also exist with using conventional cable ties.

Accordingly, what is needed in the art are improved systems for coupling tubes to ports that eliminate all or some of the above problems.

SUMMARY OF THE INVENTION

In a first independent aspect of the present invention, a method for coupling a tube to a tube fitting includes:
  radially outwardly expanding a tubular compression collar from a constricted state to an expanded state, the compression collar having a throughway extending there through and being comprised of a resiliently flexible material;
  inserting an end of a tube within the throughway of the expanded compression collar, the tube bounding a passage;
  inserting a tube fitting within the passage of the tube either before or after inserting the end of the tube within the throughway of the expanded compression collar; and
  allowing the tubular compression collar to resiliently rebound back towards the constricted state so that the compression collar pushes the tube against the tube fitting.

In one example, the step of radially outwardly expanding the tubular compression collar includes:
  inserting the prongs of an expander into the throughway of the tubular compression collar while in the constricted state; and
  radially outwardly moving the prongs so as to expand the compression collar to the expanded state.

In another example, the step of radially outwardly expanding the tubular compression collar includes:
  inserting a bladder within the throughway of the tubular compression collar while in the constricted state;
  expanding the bladder so as to expand the compression collar to the expanded state.

In another example, the step of radially outwardly expanding the tubular compression collar comprises advancing a rotating mandrel within the throughway of the tubular compression collar so that the mandrel expands the compression collar to the expanded state.

In another example, the mandrel comprises a tapered body and a plurality of rollers rotatably disposed thereon.

In another example, the step of radially outwardly expanding the tubular compression collar comprises rotating the tubular compression collar at a sufficiently high speed to cause the compression collar to expand from the constricted state to the expanded state.

In another example, the tubular compression collar comprises a tubular body having the throughway extending therethrough and a first stop lip radially inwardly projecting from the tubular body, the step of inserting the end of the tube within the throughway of the expanded compression collar comprising inserting the end of the tube into the throughway until the tube abuts the first stop lip.

In another example, the tubular compression collar comprises a tubular body having an interior surface and an opposing exterior surface that extend between a first end and an opposing second end, the interior surface bounding the throughway extending through the tubular body, a first window extends laterally through the tubular body between the interior surface and the exterior surface, the tube being visible through the window when the end of the tube is within the throughway of the expanded compression collar.

In another example, the step of inserting the tube fitting within the passage of the tube comprises inserting a tubular port of the tube fitting into the passage of the tube.

In another example, the step of inserting the tube fitting within the passage of the tube comprises inserting an annular barb of the tube fitting within the passage of the tube.

In another example, the compression collar is radially outwardly expanded without concurrently radially outwardly expanding the tube.

In another example, it takes at least 30 minutes for the compression collar to rebound so as to lose 90% of its expansion from the constricted state to the expanded state.

In another example, the throughway has a diameter, the diameter being expanded by at least 150% relative to the original constricted state as the compression collar is moved from the constricted state to the expanded state.

In another example, the tube fitting is inserted within the passage of the tube while at least a portion of the tube is disposed within the throughway of the compression collar.

In another example, the tube fitting is inserted within the passage of a portion of the tube while the portion of the tube is disposed outside of the throughway of the expanded compression collar.

In another example, gamma radiation is applied to the tubular compression collar while or after the tubular compression collar resiliently rebounds back towards the constricted state.

In another example, the tubular compression collar is comprised of high-density polyethylene (HDPE) and the step of applying the gamma radiation increases the stiffness of the compression collar.

In another example, the compression collar comprises a tubular body having the throughway extending between a first end and an opposing second end, a spacer tab outwardly projects from the first end of the tubular body, the method further comprising positioning the tube fitting so that a flange of the tube fitting butts against a terminal end of the spacer tab.

In another example, the compression collar comprises a tubular body having an interior surface that at least partially bounds the throughway, one or more compression ribs radially inwardly project from the interior surface of the body, the one or more compression ribs press against the tube when the compression collar rebounds back towards the constricted state.

In a further independent aspect of the present invention, a method for coupling a tube includes:
  radially outwardly expanding a tubular compression collar from a constricted state to an expanded state, the compression collar having a throughway extending there through and being comprised of a resiliently flexible material;
  allowing the tubular compression collar to resiliently rebound so that the tubular compression collar constricts to compress a tube against a tube fitting that are at least partially disposed within the throughway of the tubular compression collar; and
  applying radiation to the compression collar while or after the compression collar resiliently rebounds.

In one example, the tubular compression collar is comprised of a cross-linked polyethylene.

In another example, the radiation comprises gamma radiation.

In another example, the gamma radiation increasing the stiffness of the compression collar.

In a further independent aspect of the present invention, a tubular compression collar used for coupling a tube to a tube fitting includes:
  a tubular body comprised of a resiliently flexible material and having an interior surface and an opposing exterior surface that extend between a first end and an opposing second end, the interior surface bounding a throughway extending through the tubular body; and
  a first window extending laterally through the tubular body between the interior surface and the exterior surface.

In one example, the tubular body is comprised of a cross-linked polyethylene.

In another example, the first end of the tubular body terminates at a terminal end face, the first window extending through a portion of the terminal end face.

In another example, wherein the first window has an arched shaped configuration.

In another example, the first window is completely encircled by the tubular body.

In another example, a second window extends laterally through the tubular body between the interior surface and the exterior surface, the second window being spaced apart from the first window.

In another example, the second window is disposed on a side of the tubular body that is opposite the first window.

In another example, the second window is spaced apart from the first window along a length of the tubular body.

In another example, one or more spacer tabs outwardly projecting from the first end of the tubular body.

In another example, the first end of the tubular body terminates at a teiuiinal end face, the one or more spacer tabs outwardly project from the terminal end face so as to extend parallel to a longitudinal axis of the tubular body.

In another example, a first stop lip radially inwardly projecting from the tubular body at the first end.

In another example, the first end of the tubular body terminates at a terminal end face, the first stop lip radially inwardly projecting from the terminal end face.

In another example, the first stop lip radially inwardly projects from the interior surface of the compression collar.

In another example, a second stop lip radially inwardly projecting from the tubular body at the first end, the second stop lip being radially spaced apart from the first stop lip.

In another example, the throughway of the tubular body has a length extending between the first end and the opposing second end, at least a majority of the length of the throughway having a constant diameter.

In another example, one or more compression ribs radially inwardly project from the interior surface of the tubular body.

In another example, one or more annular retention ribs radially outwardly project from the exterior surface of the tubular body.

In another example, a hump is formed on and radially outwardly projects from the exterior surface of the tubular body.

In a further independent aspect of the present invention, a coupling assembly includes:
  the tubular compression collar,
  an end of a tube disposed within the throughway of the compression collar, the tube bounding a passage; and
  a tube fitting disposed within the passage of the tube, the compression collar radially inwardly compressing the tube against the tube fitting so that a liquid tight seal is formed between the tube and the tube fitting.

In one example, the tube is visible through the first window.

In another example, the tube fitting comprises a tubular stem having an annular barb formed thereon.

In another example, a first stop lip radially inwardly projecting from the tubular body at the first end thereof, a terminal end of the tube being disposed against the first stop lip.

In another example, a first spacer tab outwardly projecting from the first end of the tubular body, an end of the first spacer tab, such as a terminal end, butts against a flange of the tube fitting.

In another example, the spacer tab projects so as to extend parallel to a longitudinal axis of the tubular body.

In a further independent aspect of the present invention, a tubular compression collar used for coupling a tube to a tube fitting includes:
  a tubular body comprised of a resiliently flexible material and having an interior surface and an opposing exterior surface that extend between a first end and an opposing second end, the interior surface bounding a throughway extending through the tubular body; and
  a first compression rib radially inwardly projecting from the interior surface of the tubular body.

In one example, the first compression rib is annular and encircles the throughway.

In another example, the first compression rib does not encircle the throughway.

In another example, a second compression rib radially inwardly projects from the interior surface of the tubular body, the second compression rib being spaced apart from the first compression rib.

In another example, the second compression rib is disposed at the same location along the length of the tubular body but is radially spaced apart from the first compression rib.

In another example, the second compression rib is spaced apart from the first compression rib along the length of the tubular body.

In another example, a first stop lip radially inwardly projects from the tubular body at the first end.

In another example, one or more spacer tabs outwardly projecting from the first end of the tubular body.

In another example, the first end of the tubular body terminates at a terminal end face, the one or more spacer tabs outwardly projecting from the terminal end face so as to extend parallel to a longitudinal axis of the tubular body.

In another example, the tubular body is comprised of a cross-linked polyethylene.

In another example, one or more annular retention ribs radially outwardly project from the exterior surface of the tubular body.

In a further independent aspect of the present invention, a coupling assembly includes:
  the tubular compression collar;
  an end of a tube disposed within the throughway of the compression collar, the tube bounding a passage;
  a tube fitting disposed within the passage of the tube, the compression collar radially inwardly compressing the tube against the tube fitting so that a liquid tight seal is formed between the tube and the tube fitting, the first compression rib pressing against the tube.

In one example, the tube fitting comprises a tubular stein having an annular barb outwardly projecting therefrom.

In a further independent aspect of the present invention, a tubular compression collar used for coupling a tube to a tube fitting includes:
  a tubular body comprised of a resiliently flexible material and having an interior surface and an opposing exterior surface that extend between a first end and an opposing second end, the interior surface bounding a throughway extending through the tubular body; and
  a first spacer tab outwardly projecting from the first end of the tubular body.

In one example, the first spacer tab projects longitudinally away from the tubular body.

In another example, the first spacer tab projects parallel to longitudinal axis of the tubular body.

In another example, a second spacer tab outwardly projects from the first end of the tubular body and is spaced apart from the first spacer tab.

In another example, the first end of the tubular body terminates at a terminal end face, the first spacer tab outwardly projects from the terminal end face so as to extend parallel to a longitudinal axis of the tubular body.

In another example, the compression collar includes at least one of:
  a hump disposed on and outwardly projecting from the exterior surface of the tubular body;
  a window extending through the tubular body; and
  an annular retention rib radially outwardly projecting from the exterior surface of the tubular body.

In a further independent aspect of the present invention, a coupling assembly includes:
  the tubular compression collar;
  an end of a tube disposed within the throughway of the compression collar, the tube bounding a passage;
  a tube fitting having an outwardly projecting flange and an end disposed within the passage of the tube, the compression collar radially inwardly compressing the tube against the tube fitting so that a liquid tight seal is formed between the tube and the tube fitting.

In one example, a terminal end of the first spacer tab is butted against the flange of the tube fitting.

Each of the above independent aspects of the invention may further include any of the features, options and possibilities set out elsewhere in this document, including those associated with each of the other aspects.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
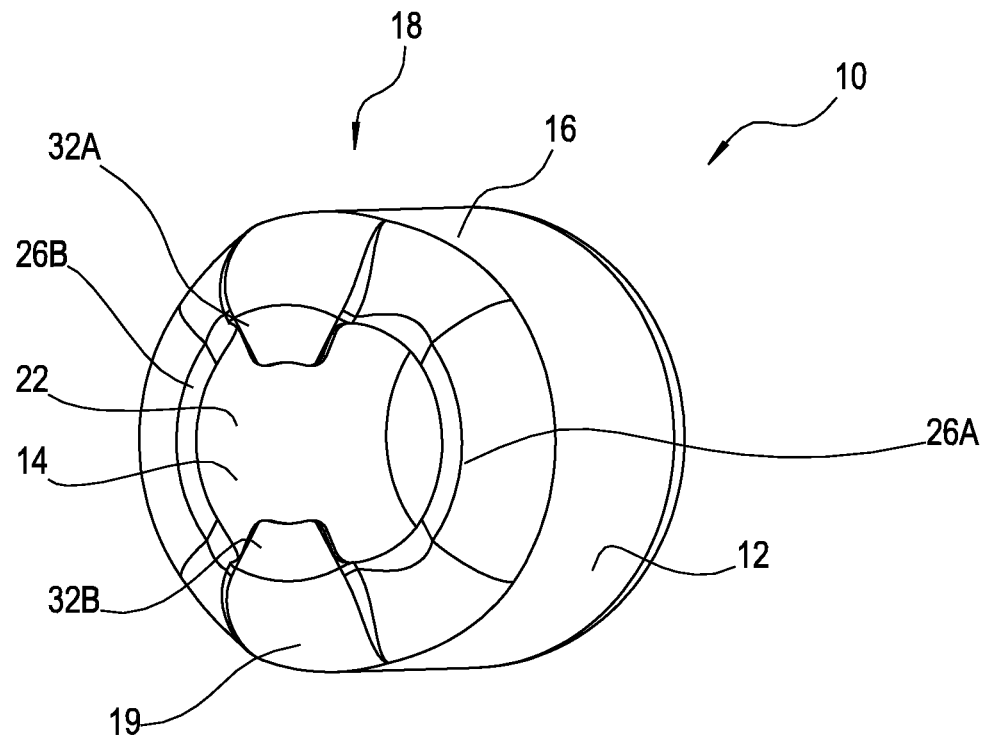
FIG. 1 is a front perspective view of a compression collar.
Figure 2:
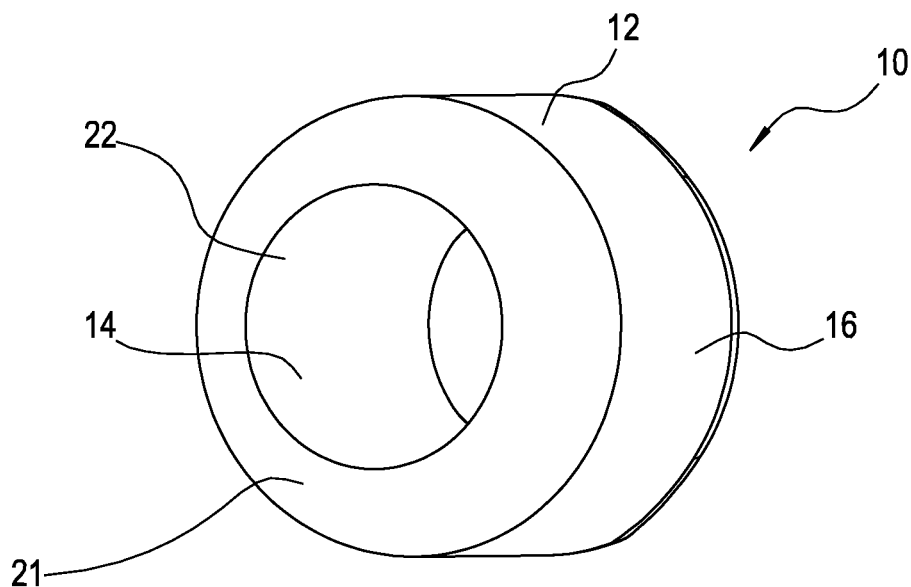
FIG. 2 is a rear perspective view of the compression collar shown in FIG. 1.

Before describing various embodiments of the present disclosure in detail, it is to be understood that this disclosure is not limited to the parameters of the particularly exemplified systems, methods, and/or products, which may, of course, vary. Thus, while certain embodiments of the present disclosure will be described in detail, with reference to specific configurations, parameters, features (e.g., components, members, elements, parts, and/or portions), etc., the descriptions are illustrative and are not to be construed as limiting the scope of the claimed invention. In addition, the terminology used herein is for describing the embodiments, and is not necessarily intended to limit the scope of the claimed invention.

Unless defined otherwise, all technical and scientific terms used herein have the same meaning as commonly understood by one of ordinary skill in the art to which the present disclosure pertains.

Various aspects of the present disclosure, including systems, processes, and/or products may be illustrated with reference to one or more embodiments or implementations, which are exemplary in nature. As used herein, the terms "embodiment" and "implementation" mean "serving as an example, instance, or illustration," and should not necessarily be construed as preferred or advantageous over other aspects disclosed herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "stop lip" includes one, two, or more stop lips.

As used herein, directional terms, such as "top," "bottom," "left," "right," "up," "down," "upper," "lower," "proximal," "distal" and the like are used herein solely to indicate relative directions and are not otherwise intended to limit the scope of the disclosure and/or claimed invention.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

To facilitate understanding, like reference numerals (i.e., like numbering of components and/or elements) have been used, where possible, to designate like elements common to the figures. Specifically, in the exemplary embodiments illustrated in the figures, like structures, or structures with like functions, will be provided with similar reference designations, where possible. Specific language will be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential). Furthermore, multiple instances of an element and or sub-elements of a parent element may each include separate letters appended to the element number. Furthermore, an element label with an appended letter can be used to designate an alternative design, structure, function, implementation, and/or embodiment of an element or feature without an appended letter. Likewise, an element label with an appended letter can be used to indicate a sub-element of a parent element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where multiple possibilities of values or a range a values (e.g., less than, greater than, at least, or up to a certain value, or between two recited values) is disclosed or recited, any specific value or range of values falling within the disclosed range of values is likewise disclosed and contemplated herein. Thus, disclosure of an illustrative measurement or distance less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 unit, between 8 units and 2 units, between 6 units and 4 units, and/or any other range of values between 0 and 10 units.

The headings used herein are for organizational purposes only and are not meant to be used to limit the scope of the description or the claims.

Reference will now be made to the figures of the present disclosure. It is noted that the figures are not necessarily drawn to scale and that the size, orientation, position, and/or relationship of or between various components can be altered in some embodiments without departing from the scope of this disclosure.

Depicted in FIGS. 1-4 is one embodiment of a compression collar 10 incorporating features of the present invention. Compression collar 10 comprises a tubular body 12 having an interior surface 14 and an opposing exterior surface 16 that extend between a first end 18 and an opposing second end 20. First end 18 terminates at a terminal end face 19 while second end 20 terminates at a terminal end face 21.

Interior surface 14 bounds a throughway 22 that extends through body 12 between first end 18 and second end 20. Throughway 22 typically has a circular transverse cross section. With the exception of the location of stop lips, as discussed below, throughway 22 can have a constant diameter D extending along the length of body 12. In other embodiments, interior surface 14 can outwardly flare at second end 20 to assist in easy and guided insertion of a tube within throughway 22 from second end 20. As such, diameter D of throughway 22 will typically have a constant diameter over at least or less than 40%, 60%, 80%, 90%, 95%, or 98% of the length of throughway 22 or in a range between any two of the foregoing.

Compression collar 10 can be formed having a variety of different sizes depending on intended use and depending on the size of the tube to be used with compression collar 10. In some embodiments, the maximum diameter D can be at least or less than 4 mm, 6 mm, 8 mm, 10 mm, 15 mm, 20 mm, 25 mm, 30 mm, 40 mm or in a range between any two of the foregoing. Other dimensions can also be used. Compression collar 10 can also have a length $L_1$ extending between end faces 19 and 21 that can be at least or less than 4 mm, 6 mm, 8 mm, 10 mm, 15 mm, 20 mm, 25 mm, 30 mm, 40 mm or in a range between any two of the foregoing. Other dimensions can also be used.

In the depicted embodiment, body 12 is formed having a pair of windows 26A and 26B. More specifically, window 26A extends laterally through body 12 from exterior surface 16 to interior surface 14 at first end 18 so as to communicate with throughway 22. In the depicted embodiment, window 26A also extends through or is recessed into terminal end face 19. Window 26A is partially bounded by a recessed surface 28 having an arched configuration. The arched configuration can be elongated, as depicted, or can be semi-circular, U-shaped, C-shaped or have other arched shaped configurations. Window 26B has the same design and configuration of window 26A except that it is formed on the opposing side of body 12 at first end 18. All elements and alternatives discussed with window 26A are also applicable to window 26B. As discussed below in greater detail, windows 26 enable visual inspection to tubes or other structures that may be received within throughway 22.

Although body 12 is shown as having two opposing windows 26, in alternative embodiments, body 12 can be formed with at least or less than one window, two windows, three windows, four windows and any other desired number of windows. In addition, windows need not be arched but could have other configuration that recess into terminal end face 19 and pass through body 12. For example, windows 26 could comprise a notch having the shape of a V, square, rectangle, polygon, square, linear slot, or other configurations. In addition, windows 26 need not be positioned on opposing sides of body 12 but can be merely spaced apart. In still other embodiments, windows 26 need not be recessed into end face 19 but could be spaced back from end face 19 so that the one or more windows 26 form an aperture extending through body 12 that is completely encircled by body 12. Again, any desired shape could be used for such windows and any of the above desired numbers of windows can be formed.

Figure 3:
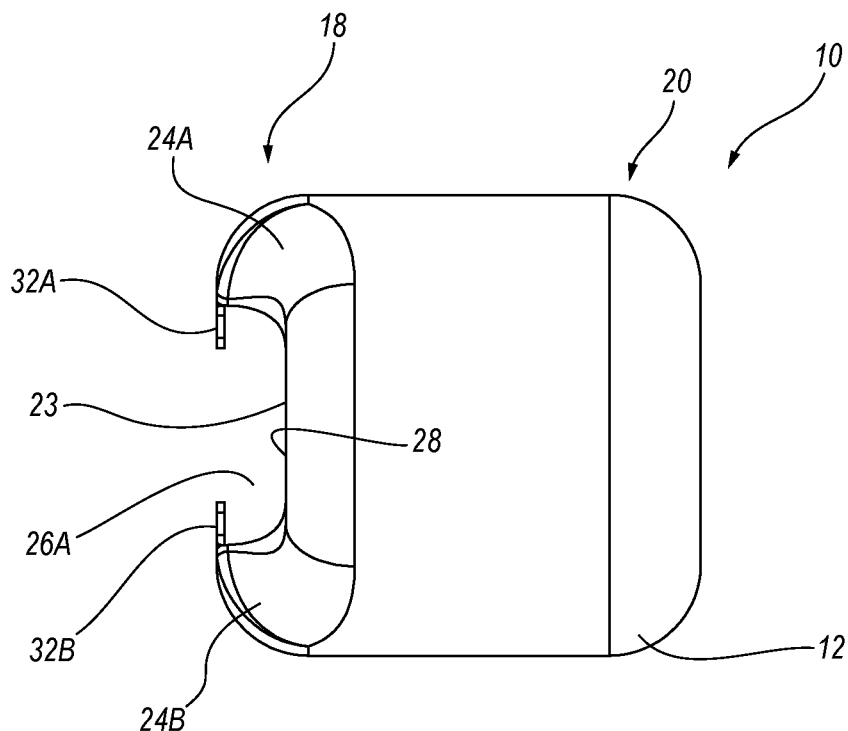
FIG. 3 is an elevated side view of the compression collar shown in FIG. 1.
Figure 4:
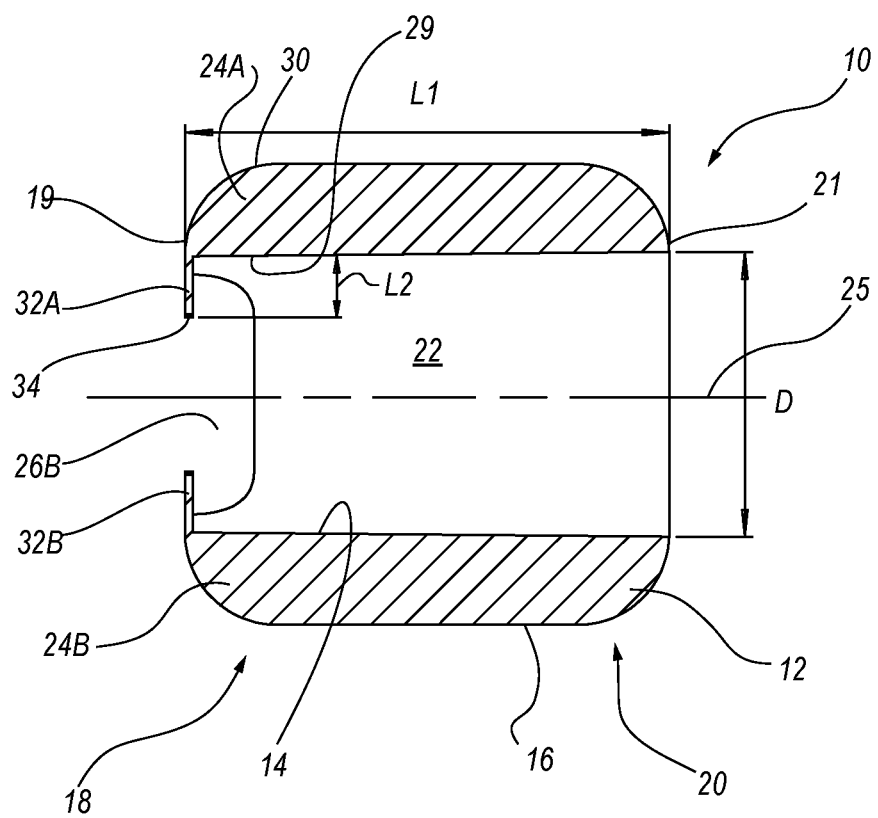
FIG. 4 is a cross sectional side view of the compression collar shown in FIG. 1.

As also depicted in FIGS. 1, 3, and 4, compression collar 10 can comprise a pair of stop lips 32A and 32B. Specifically, stop lip 32A radially inwardly projects at first end 18 of body 12 so as to be aligned with and/or disposed within throughway 22. That is, stop lip 32A can radially inwardly project from interior surface 14 at first end 18 into throughway 22 or can be mounted on terminal end face 19 and inwardly project so as to be aligned with throughway 22. Stop lip 32A typically has a length $L_2$ projecting into throughway 22, i.e., the length extending between body 12 and a terminal tip 34, that is at least or less than 2%, 5%, 10%, 15%, 20% or 25% of the diameter D of throughway 22 adjacent to stop lip 32A or is in a range between any two of the foregoing. As discussed below in more detail, stop lip 32A functions as a stop for a tube or other structure being inserted into throughway 22 from second end 20 so that the tube or other structure is properly positioned within compression collar 10.

Stop lip 32B can have the same configuration, dimensions and relative positioning as stop lip 32A except that stop lip 32B is spaced apart from stop lip 32B. More commonly, stop lip 32B is typically disposed on the opposing side of body 12 so that stop lips 32A and 32B project inwardly towards each other. Stop lips 32A and 32B can also be disposed in a common plane. In the depicted embodiment, two stop lips 32A and 32B are shown. In an alternative embodiment, at least or less than one, two, three, four or more stop lips 32 can be disposed on body 12. Furthermore, in the depicted embodiment stop lips 32A and 32B are shown at or directly adjacent to terminal end face 19. In other embodiments, the one or more stop lips can be formed on interior surface 14 at a location spaced away from terminal end face 19 and toward second end 20. In other embodiments, stop lips 32 can be eliminated. As such, first end 18 could be formed only having the one or more windows 26 formed thereon and no stop lips 32 or could be formed only having the one or more stop lips 32 formed thereon and no windows 26. In yet other embodiments, both stop lips 32 and windows 26 can be eliminated so that first end 18 can have the same configuration as second end 20.

It is appreciated that compression collar 10 can also be described in a slightly alternative way. For example, in the above discussion compression collar 10 comprises tubular body 12 that extends between end faces 19 and 21 while windows 26A and 26B extend laterally through body 12 at first end 18. In contrast, however, with continued reference to FIGS. 1-4, compression collar 10 can also be described as comprising tubular body 12 that extends between an annular terminal end face 23 at first end 18 and annular terminal end face 21 at second end 20. A pair of spacer tabs 24A and 24B outwardly project from terminal end face 23. In the depicted embodiment, spacer tabs 24 project so as to extend parallel to a longitudinal axis 25 of tubular body 12 and more specifically to a central longitudinal axis 25 of throughway 22. Spacer tabs 24A and 24B are spaced apart and project from opposing sides of terminal end face 23 so that throughway 22 is disposed therebetween. Each spacer tab 24 has an interior surface 29 and an opposing exterior surface 30 that extend to terminal end face 19, that was previously referenced.

Although not required, in one embodiment interior surface 29 can extend flush with and continuously with interior surface 14 of tubular body 12. Stop lips 32A and 32B radially inwardly project from spacer tabs 24A and 24B, respectively. Stop lips 32 can project from interior surface 29 or terminal end face 19 of spacer tabs 24A and 24B. In contrast to describing windows 26A and 26B as passing through tubular body 12, windows 26A and 26B are now described as begin bounded by the opposing ends of spacer tabs 24A and 24B and being bounded on one side by terminal end face 23 of tubular body 12.

Compression collar 10 is typically comprised of a polymeric material having memory properties, i.e., the material will resiliently rebound towards its original shape when stretched. One common example of a polymeric material having memory properties that can be used to form compression collar 10 is cross-linked polyethylene that is commonly abbreviated as PEX. PEX is commonly formed from high-density polyethylene (HDPE). PEX contains cross-linked bonds in the polymer structure that change the thermoplastic to a thermoset. Depending on the manufacturing process and the specific type of material used to form compression collar 10, the cross-linking can be accomplished prior to, during or after the forming of compression collar 10. The required degree of cross-linking is typically between 65% and 89%. A higher degree of cross-linking could result in brittleness and stress cracking of the material, while a lower degree of cross-linking could result in product with poor physical properties.

For some cross-linking materials, e.g. some HDPE materials, the cross-linking or at least a majority of the cross-linking can automatically be achieved during the manufacture process, especially where the material forming the compression collar is heated during the forming process. A Silane or "moisture cure" method can also be used to further facilitate the desire cross-linking. In this method, the formed compression collars are placed in a heated water bath or in a heated environmental chamber having a relative humidity of between 60% and 98% and allowed to cure for a sufficient time to achieve the desired cross-linking. Other applications of heat and moisture can also facilitate the needed cross-linking.

For some alternative cross-linking materials, the cross-linking can be accomplished by applying radiation, such as electron beam radiation (ebeam), to the polymer, as is commonly known in the art. For example, in one method of cross-linking the polymer, compression collar 10 is subject to at least or less than 50 kGy, 60 kGy, 70 kGy or 80 kGy of ebeam or in a range between any two of the foregoing, after being molded. Other amounts can also be used.

In one method of manufacture, compression collar 10 can be formed by a molding process such as injection molding. The injection molding process heats the material which can facilitate at least a majority of the needed cross-linking Using an injection molding process enables the compression collar 10 to be easily formed with rounded corners so as to avoid or limit sharps. Typically, compression collar 10 will be molded and then subjected to post cross-linking process, such as discussed above. However, the desired cross-linking can be achieved during the initial manufacturing process either as a result of the manufacture process and/or by applying heat and/or humidity during manufacture and/or applying radiation during manufacture. It is appreciated that other molding processes such as blow molding, rotational molding, and the like can also be used to form compression collar 10. Other manufacturing processes can also be used to form compression collar 10. For example, compression collar 10 could be machined or cut from an extruded tube of material. Other methods can also be used.

Figure 5:
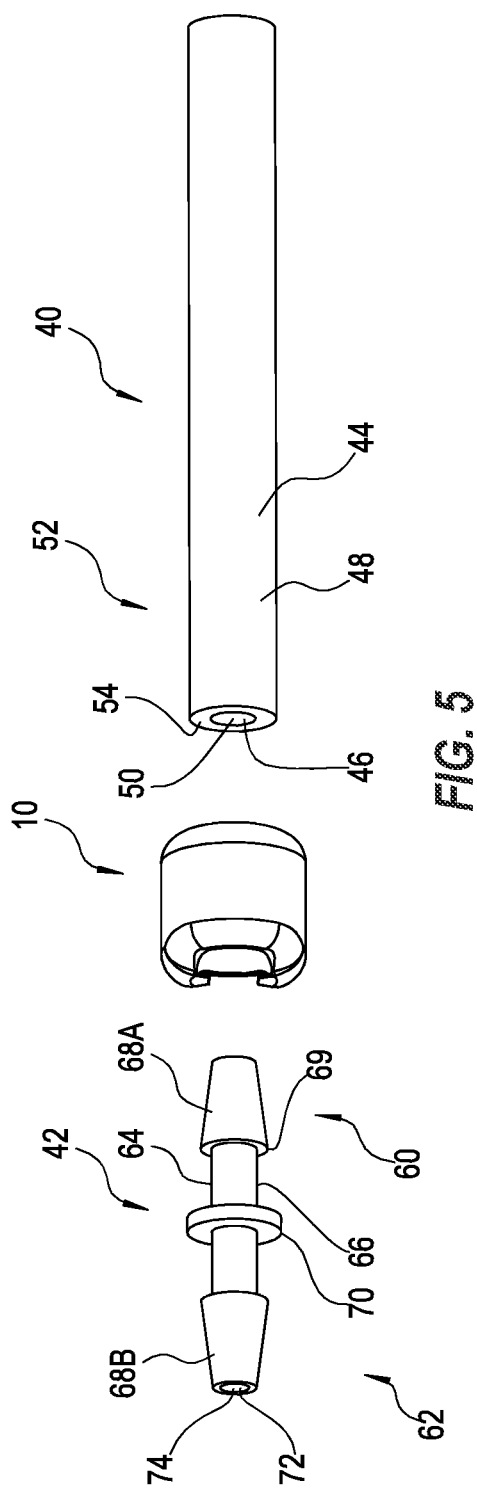
FIG. 5 is an exploded view showing the compression collar of FIG. 1, a tube, and a tube fitting.

As depicted in FIG. 5, compression collar 10 can be used to secure a tube 40 to a tube fitting 42 so that a liquid tight seal is formed between tube 40 and tube fitting 42. More specifically, tube 40 comprises an encircling side wall 44 having an interior surface 46 and an opposing exterior surface 48. Interior surface 46 bounds a passage 50 extending along the length of tube 40. Tube 40 has a first end 52 that terminates at a terminal end face 54. Tube 40 is also typically made of a polymeric material having memory properties. Although in some embodiments tube 40 can be made of the same material as compression collar 10, as discussed above, tube 40 is commonly made from a material that is different from the material for compression collar 10. Typically, the material for tube 40 has a modulus of elasticity that is lower than the modulus of elasticity for the material of compression collar 10. That is, the material for tube 40 is typically more flexible than the material used to form compression collar 10. Examples of materials that can be used for tube 40 that have a lower modulus of elasticity include silicone, polyvinyl chloride (PVC), and thermoplastic elastomers (TPE). Other materials can also be used. It is appreciated that tube 40 can have any desired diameter and any desired length.

The term "tube fitting" as used in the specification and appended claims is broadly intended to include any type of fitting or other structure designed for coupling with tube 40. For example, tube fitting 42 could comprise a coupling fitting, union fitting, port fitting, plug fitting, T-fitting, Y-fitting, elbow fitting, reducer fitting, adapter fitting or the like. Tube fitting 42 may be a standalone structure or may be attached to or be configured to be attach to another structure such as a bag, container, tube, or other fitting. Commonly, at least a portion of tube fitting 42 is designed to be received within passage 50 of tube 40 for making a connection therewith. It is also common that tube fitting 42 is tubular so that a sealed fluid connection can be formed between tube fitting 42 and tube 40. In other embodiments, however, such as where tube fitting 42 is a plug, tube fitting 42 need not be tubular.

In the depicted embodiment, tube fitting 42 comprises a coupling fitting used to fluid couple two separate tubes together. Tube fitting 42 comprises a stem 64 having a first end 60 and an opposing second end 62. Formed on and radially encircling exterior surface 66 of stem 64 at first end 60 is an annular barb 68A having a frustoconical configuration. Barb 68A includes an annular outside shoulder 69. Although stem 64 is shown having a single barb 68A formed thereon, in other embodiment, stem 64 can be formed with at least or less than one, two, three, four or more consecutive or spaced apart barbs 68A formed thereon. Formed on and radially encircling exterior surface 66 of stem 64 at second end 62 is an annular barb 68B having the same configuration and elements as barb 68A. Again, stem 64 can be formed with at least or less than one, two, three, four or more barbs 68B formed thereon. Although not required, a flange 70 encircles and radially outwardly extends from stem 64 at a location between barbs 68A and 68B. As also shown in FIG. 5, stem 64 can be tubular having an interior surface 72 that bounds a passage 74 that extends through stem 64 between opposing ends 60 and 62.

Tube fitting 42 is typically molded from a polymeric material. However, other materials and molding processes can also be used. Tube fitting 42 is also typically made from a material that is different from the material used to form tube 40 and compression collar 10. In addition, the material used to form tube fitting 42 typically has a modulus of elasticity that is greater than the modulus of elasticity of the materials used to form tube 40 and compression collar 10. That is, tube fitting 42 is typically less flexible than tube 40 and compression collar 10.

Figure 6:
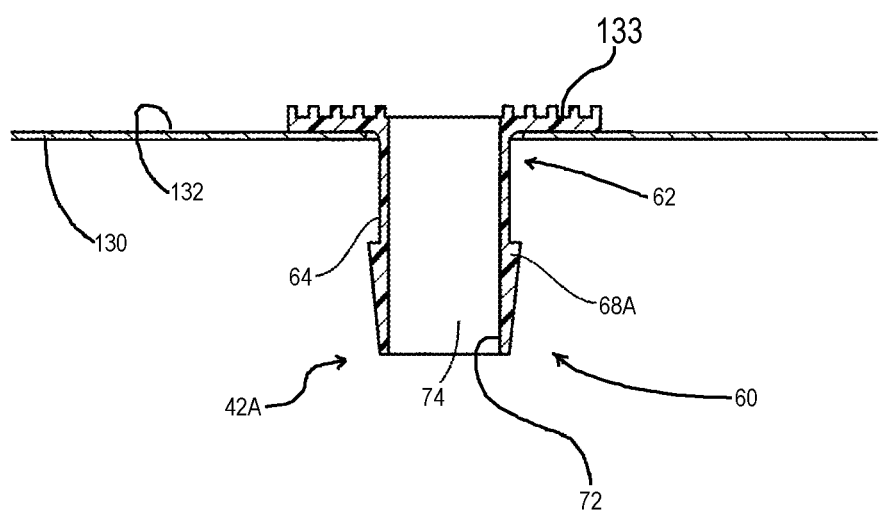
FIG. 6 is a perspective view of an alternative embodiment of a tube fitting coupled to a container.

As previously discussed, tube fitting 42 can have a variety of different configurations. For example, depicted in FIG. 6 is one example of tube fitting 42A that comprises a port fitting and is coupled to a container 130. Like elements between tube fittings 42 and 42A are identified by like reference characters. Tube fitting 42A includes tubular stem 64 having annular barb 68A formed on first end 60 thereof. The alternative number of barbs 68A as discussed above with regard to tube fitting 42 are also applicable to tube fitting 42A. In contrast to tube fitting 42, tube fitting 42A has second end 62 with a flange 133 outwardly projecting therefrom. In this embodiment, flange 133 is secured to an interior surface 132 of container 130 such as by welding or adhesive. Stem 64 extends through an opening in container 130.

Container 130 can comprise a rigid, semi-rigid or flexible container. For example, container 130 can comprise a collapsible, flexible bag made from one or more sheets of polymeric film. The polymeric film can comprise a flexible, water impermeable material, such as a low-density polyethylene, and may have a thickness that is at least or less than 0.02 mm, 0.05 mm, 0.1 mm, 0.2 mm, 0.5 mm, 1 mm, 2 mm, 3 mm or in a range between any two of the foregoing. The film is may be sufficiently flexible that it can be rolled into a tube without plastic deformation and/or can be folded over an angle of at least 90°, 180°, 270°, or 360° without plastic deformation. Other materials can also be used.

Figure 7:
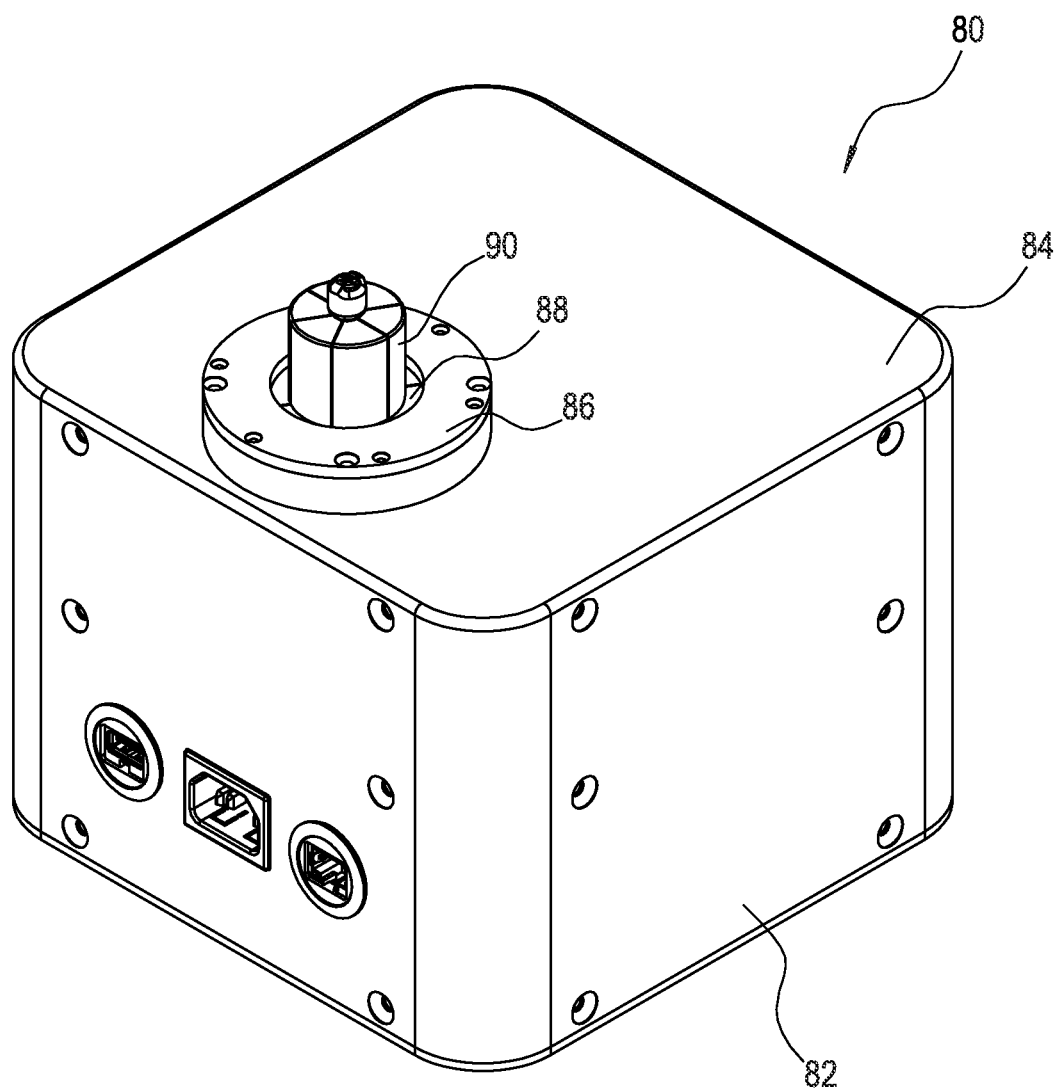
FIG. 7 is a perspective view of an expander.
Figure 8A:
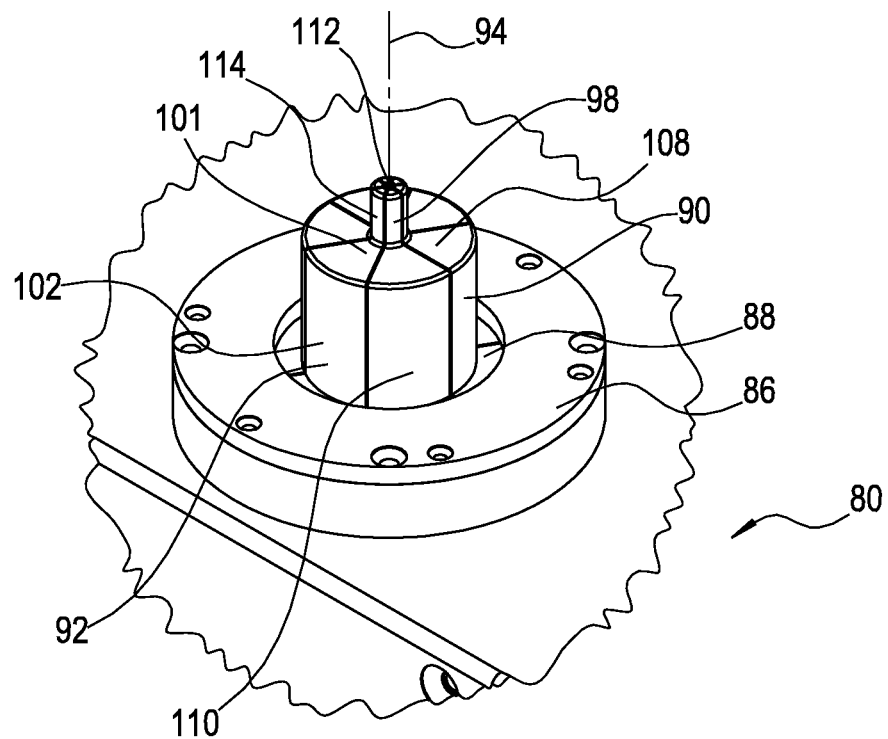
FIG. 8A is an enlarged perspective view of the expansion mechanism of the expander shown in FIG. 7 with the expansion mechanism in collapsed position.
Figure 8B:
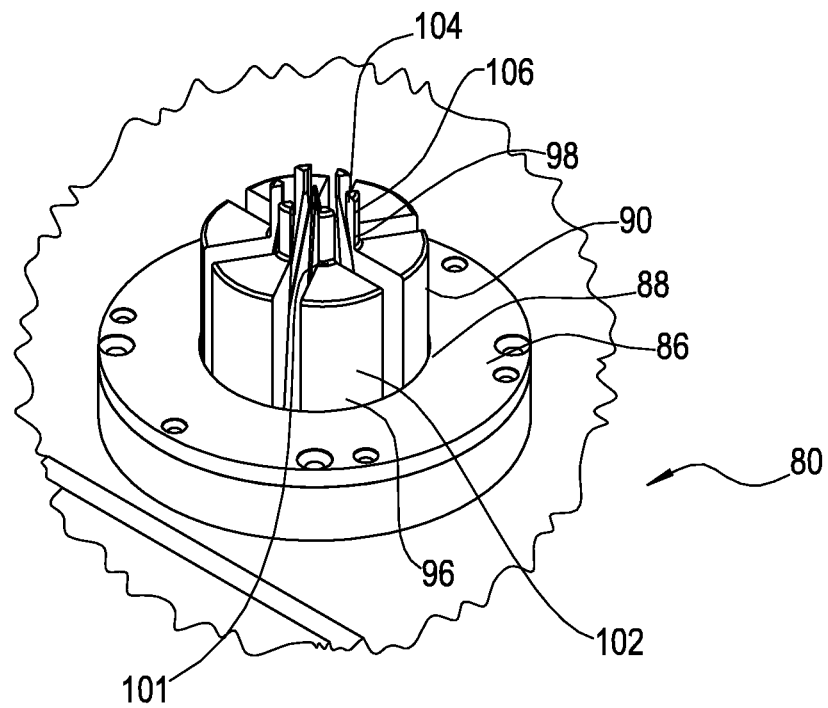
FIG. 8B is a perspective view of the expansion mechanism shown in FIG. 8A in an expanded position.

When using compression collar 10 to secure tube fitting 42 to tube 40, compression collar 10 is first expanded from an initial constricted state to an expanded state. As depicted in FIG. 7, compression collar 10 can be expanded using an expander 80. In general, expander 80 comprises a housing 82 having a top surface 84 with an annular stop ring 86 disposed thereon. Stop ring 86 encircles and opening 88 extending therethrough. Disposed within opening 88 is an expansion mechanism 90. As depicted in FIGS. 8A and 8B, expansion mechanism 90 comprises a plurality of elongated fingers 92 that are radially spaced about a common central axis 94. In general, each finger 92 comprises an elongated base 96 and an elongated prong 98 outwardly projecting from each base 96. More specifically, each base 96 has a wedge or pie shaped cross sectional configuration with a top face 100 that extends between a constricted inside end 101 and an opposing widened outside face 102. Top face 100 is shown as being flat while widened outside face 102 is rounded or arced. Each prong 98 upwardly projects from top face 100 of each base 96 at constricted inside end 101. Each prong 98 also has a wedge or pie shaped cross sectional configuration that extends between a constricted inside end 104 and a widened outside face 106. Outside face 106 is rounded or arced.

Fingers 92 can move between a collapsed position, as shown in FIG. 8A, and an expanded position, as shown in FIG. 8B. In the collapsed position fingers 92 move together so as to encircle a common central axis 94. More specifically, bases 96 combine to form a cylinder having a central axis 94 that includes a flat, circular, top surface 108 and a cylindrical side wall 110. Prongs 98 also concurrently move together to form a cylinder having the same central axis 94 that includes a flat, circular, top surface 112 and a cylindrical side wall 114.

As fingers 92 move from the collapsed position of FIG. 8A to the expanded position of FIG. 8B, each base 96 and prong 98 moves radially outward away from central axis 94. Fingers 92 move outwardly until they hit against stop ring 86. Stop ring 86 thus prevents fingers 92 from expanding farther than desired.

In the depicted embodiment, expansion mechanism 90 includes six fingers 92 and thus six bases 96 and six prongs 98. In alternative embodiments, it is appreciated that expansion mechanism 90 can be formed with at least or less than 2, 3, 4, 5, 6, 7, 8, 9, or 10 fingers 92 and a corresponding number of bases 96 and prongs 98. The number of fingers 92 can also be in the range between any two of the foregoing numbers. Other numbers of fingers 92 could also be used. It is appreciated that any form of drive mechanism, such as a gear drive, pneumatic drive, hydraulic drive, belt drive and the like, can be used to move fingers 92 between the collapsed and expanded positions. It is also appreciated that expander 80 is only one example of an expander that can be used to expand compression collar 10. It is appreciated that any form of expander that will function of expand compression collar 10, as discussed below, can be used in the methods of the present invention.

Figure 9:
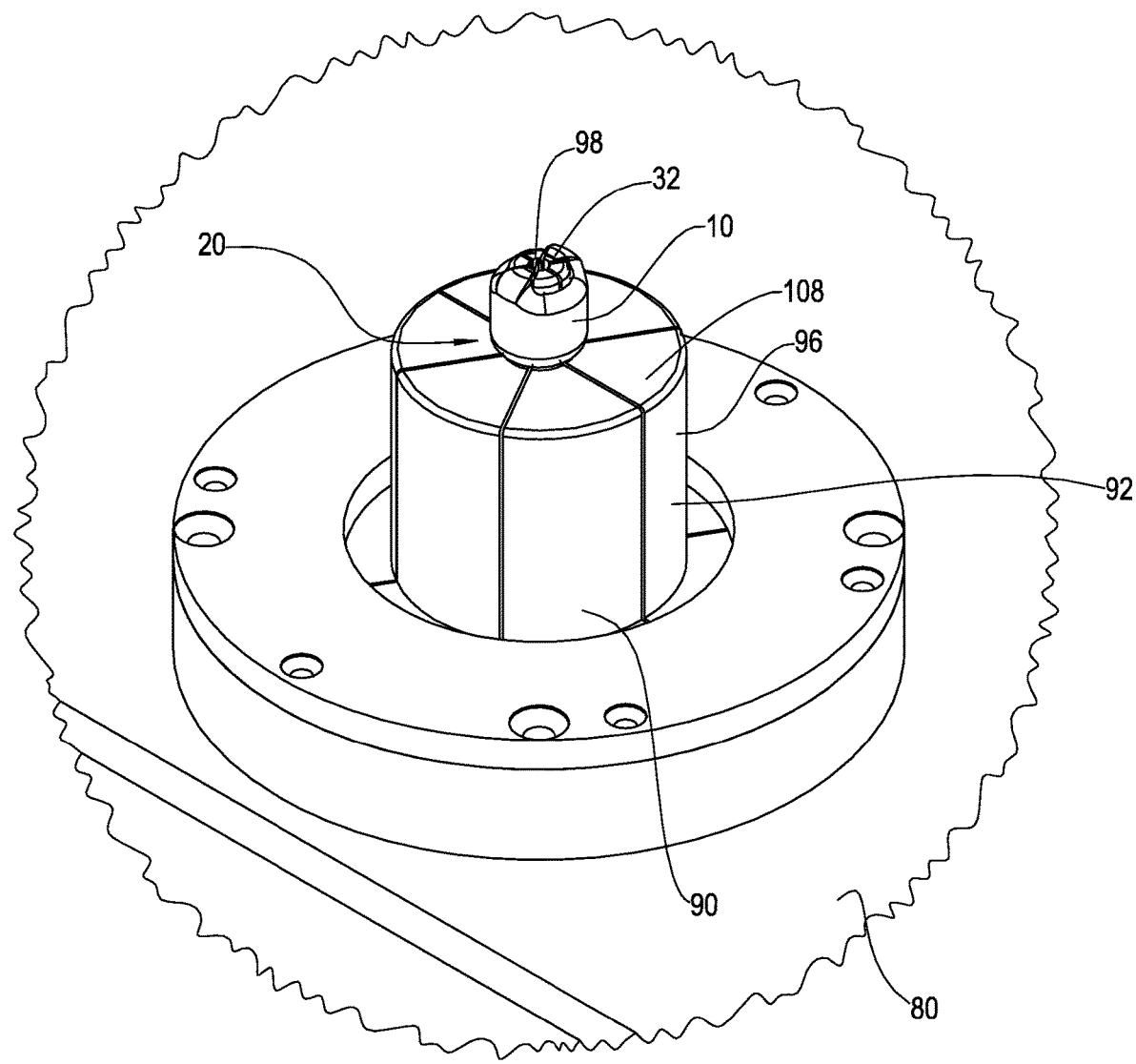
FIG. 9 is a perspective view of the expansion mechanism of FIG. 8A with the compression collar of FIG. 1 disposed thereon.

During use, expansion mechanism 90 is initially moved to the collapsed position. As depicted in FIG. 9, second end 20 of compression collar 10 is then advanced over prongs 98 so that prongs 98 are received within throughway 22 (FIG. 4). Compression collar 10 can be advanced until stopped by the free end of prongs 98 hitting against stop lips 32 and/or second end 20 of compression collar 10 hitting against top surface 108 of bases 96. In either event, prongs 98 extend the full length or substantially the full length of throughway 22. For example, prongs 98 can extend at least 80%, 90%, 95% or 98% of the full length of throughway 22. Once compression collar 10 is properly positioned on prongs 98, fingers 92 are moved radially outward to the expanded position, as shown in FIG. 8B, thereby radially stretching compression collar 10 from its constricted state to its expanded state.

Once compression collar 10 is stretched to the expanded state, fingers 92 are again moved back toward the retracted position so that compression collar 10 can be freely removed from fingers 92. Compression collar 10 begins to automatically, resiliently rebound back toward its constricted state as soon as it is released from prongs 98. Compression collar 10 will typically rebound to lose 50% of its expansion within 30 second of being released. Because of the mechanical properties of compression collar 10, however, it will typically take at least 30 minutes and more commonly at least 1 hour or 2 hours for compression collar 10 to rebound so as to lose 90% of its expansion. The time for rebounding is in part dependent upon the extent of the original stretching. In the present invention, a compression collar 10 of a set size may stretched to different ratios depending on its intended use. In some uses, compression collars disclosed herein are typically expanded to at least or less than 115%, 130%, 140%, 150%, 160%, 180%, 200%, 210% of their original constricted diameter or in a range between any two of the forgoing. For example, the diameter D in FIG. 4 can be expanded to the foregoing percentages. Other values can also be used. Furthermore, there may be some plastic deformation of compression collar 10 in the original stretching. As such, compression collar 10 may not be able to fully return to its original constricted state.

It is appreciated that the use of expander 80 is only one of many methods that can used to expand compression collar 10. By way of example and not by limitation, compression collar 10 could also be expanded by inserting a bladder, either elastomeric or non-elastomeric, within throughway 22 and then expanding the bladder to expand compression collar 10. In another method, compression collar 10 can be rapidly spun to produce expansion by centrifugal force. In still another method, a tapered punch could be linearly pressed into throughway 22 for expanding compression collar 10. As discussed below in further detail, in still other methods, a tapered mandrel can be rotated and advanced within throughway 22 to expand compression collar 10. Rollers or air bearings could be disposed on the mandrel to reduce friction and damage to the compression collar. Other methods can also be used.

Figure 10A:
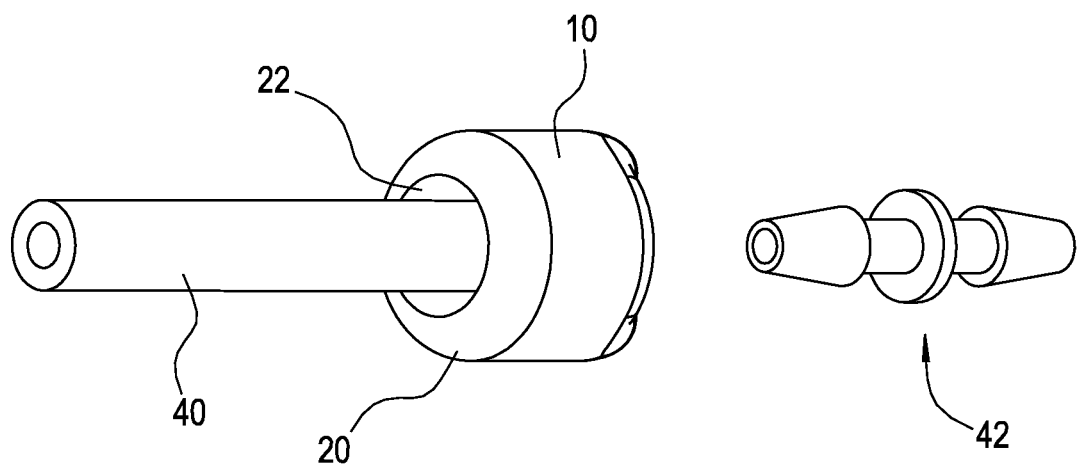
FIG. 10A is a rear perspective view of the tube of FIG. 5 received within the expanded compression collar.
Figure 10B:
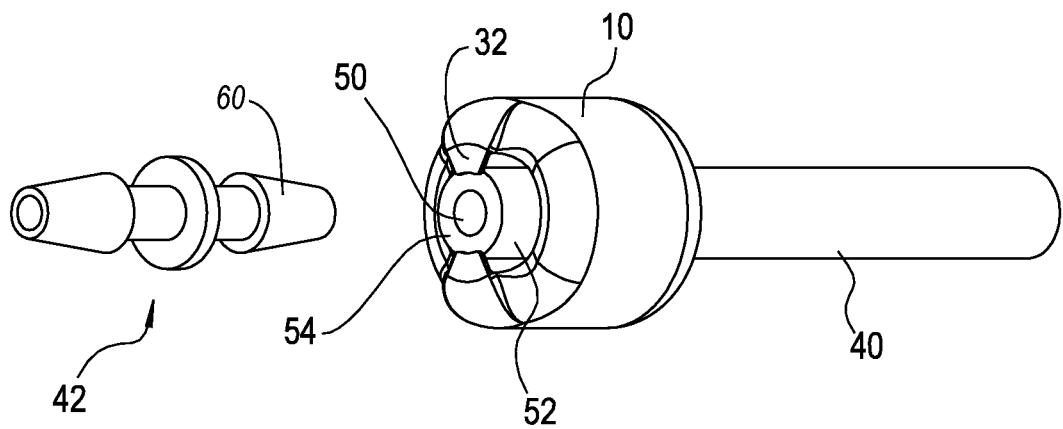
FIG. 10B is a front perspective view of the assembly shown in FIG. 10A.

Turning to FIGS. 10A and 10B, once compression collar 10 is in the expanded state, first end 52 of tube 40 is advanced into throughway 22 of compression collar 10 until first end 52 butts against one or both of stop lips 32. Stop lips 32 thus help to properly position tube 40 within compression collar 10.

Figure 11:
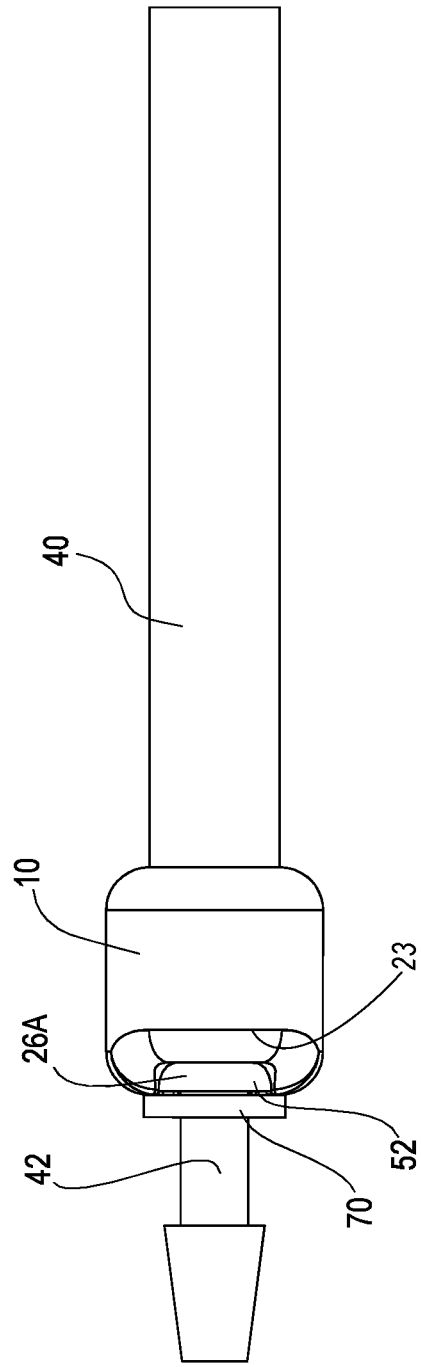
FIG. 11 is elevated side view of the assembled tube fitting, tube, and compression collar shown in FIG. 5.
Figure 12:
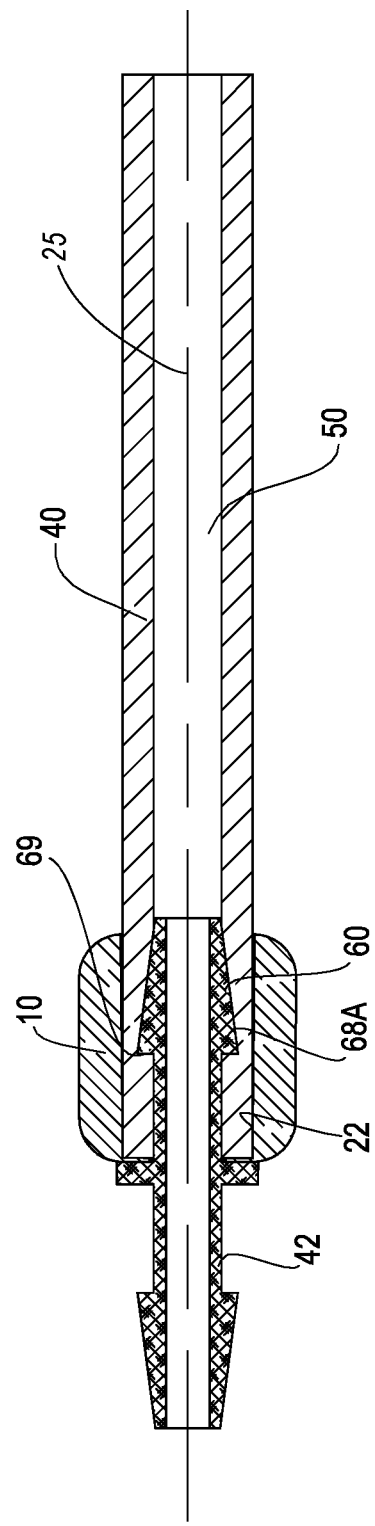
FIG. 12 is a cross sectional side view of the assembly shown in FIG. 11.

As depicted in FIGS. 11 and 12, once tube 40 is properly positioned within compression collar 10, first end 60 of tube fitting 42 is advanced into passage 50 of tube 40 at first end 52 while tube 40 is supported within compression collar 10. Tube fitting 42 is typically advanced into passage 50 prior to significant constricting of compression collar 10 so that compression collar 10 does not interfere with the insertion of tube fitting 42. Furthermore, tube 40 is typically sufficiently flexible that tube fitting 42 can be manually pressed into passage 50. In other embodiments, however, a tool or machine can be used to assist in the insertion of tube fitting 42.

In the depicted embodiment, tube fitting 42 is advanced until flange 70 butts against compression collar 10. Windows 26 enable a visual inspection of first end 52 of tube 40 to ensure that first end 52 remains adjacent to or butted against the interior surface of stop lips 32 while flange 70 is positioned adjacent to or butted against the opposing exterior surface of stop lips 32, thereby ensuring that both tube 40 and tube fitting 42 are properly positioned within compression collar 10.

Once tube 40 and tube fitting 42 are properly positioned, compression collar 10 is left to automatically, resiliently rebound back toward the constricted state. At a minimum, compression collar 10 resiliently rebounds so as to have an inner diameter that is smaller than the outer diameter of tube 40, thereby compressing tube 40. As compression collar 10 resiliently constricts, it radially inwardly pushes and constricts tube 40, as depicted in FIG. 12, so as to form a uniform, annular, liquid tight seal between tube 40 and barb 68A. Here it is noted that compression collar 10 is sized relative to tube 40, as depicted in FIG. 10B, so that when compression collar 10 is in the expanded state, terminal end face 54 of tube 40 necessarily butts against one or both of stop lips 32 when advanced through throughway 22, as opposed to freely passing between stop lips 32. However, compression collar 10 is also configured so that tube fitting 42 can be advanced into passage 50 of tube 40 without significant interference by stop lips 32 of compression collar 10. That is, tube fitting 42 may cause bending or flexing of stop lips 32 as tube fitting 42 is advanced into passage 50 of tube 40 but stop lips 32 will not preclude coupling of tube fitting 42 and tube 40. Likewise, compression collar 10 is configured so that stop lips 32 do not prematurely hit against tube fitting 42, thereby preventing compression collar 10 from properly compressing tube 40 about barb 68.

It is appreciated that a single compression collar 10 can be used with a plurality of different tubes 40 having different diameters within a fixed range of diameters. For tubes 40 outside of the range of diameters, a different sized compression collar 10 can be used. As such a plurality of different sized compression collars 10 can be produced where each compression collar 10 is designed to be used with a plurality of different tubes 40 having different diameters within a fixed range of diameters.

As also depicted in FIG. 12, tube fitting 42 is typically positioned so that shoulder 69 of barb 68A is centrally positioned along the length of throughway 22 of compression collar 10. More specifically, shoulder 69 is typically positioned so as to be located at a distance from the center of the length of throughway 22, i.e., central axis 25, that is less than or at least 2%, 4%, 6%, 8%, 10%, 12%, 15%, 20%, 30%, or 40% of the length of throughway 22. Other positioning can also be used.

In an alternative embodiment where compression collar 10 does not include stop lips 32, it is appreciated that tube 40 could first be passed all the way through expanded compression collar 10. Tube fitting 42 could then be pressed within passage 50 of tube 40 so the tube fitting 42 still remains outside of compression collar 10. The combined tube 40 and tube fitting 42 could then be received within throughway 22 of compression collar 10 for being radially compress by compression collar 10.

Although not required, in one embodiment of the present invention, after compression collar 10 has rebounded toward the contracted state so as to compress tube 40 and produce the seal between tube 40 and tube fitting 42, radiation, such as gamma radiation, can be applied to the assembled compression collar 10, tube fitting 42 and tube 40. It is theorized that the applied radiation further increases the cross linking of the polyethylene or other material used to form compression collar 10. By increasing the cross linking, compression collar 10 becomes stiffer, thereby further securing the connection between tube fitting 42 and tube 40. This increased connection helps to prevent any unintentional separation or leaking between tube fitting 42 and tube 40 as tube fitting 42 and/or tube 40 are subsequently moved, such as during shipping or use. The application of such radiation prior to the expansion of compression collar 10 may not be desirable because it could make compression collar 10 too rigid for proper expansion. However, applying the radiation after rebounding of the compression collar 10 helps to solidify the secure the engagement between tube fitting 42 and tube 40. In some methods, the radiation can be applied while and/or after the compression collar 10 is resiliently rebounding toward the constricted state.

It is noted that in the above discussed method of assembly that compression collar 10 is moved from the constricted to expanded state independent of tube 40. That is, tube 40 is not concurrently expanded with compression collar 10. Rather, compression collar 10 first expanded and then tube 40 is inserted into the expanded compression collar 10 while tube 40 is in it normal unexpanded state. However, in some embodiments, it may be desirable to first insert tube 40 into compression collar 10 and then currently expand both tube 40 and compression collar 10 using expander 80 or some other expander. Tube fitting 42 can then still be received within tube 40 as discussed above.

Figure 13:
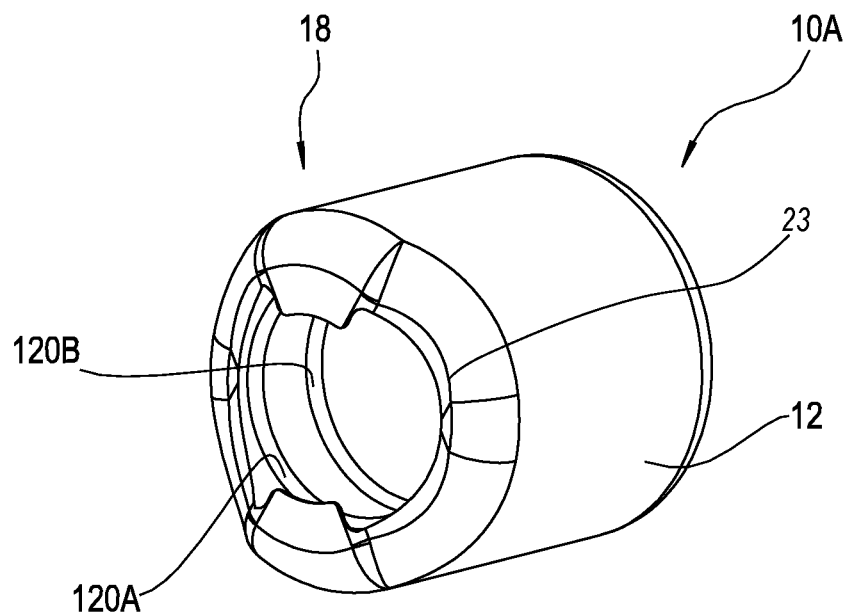
FIG. 13 is a front perspective view of an alternative embodiment of a compression collar.
Figure 14:
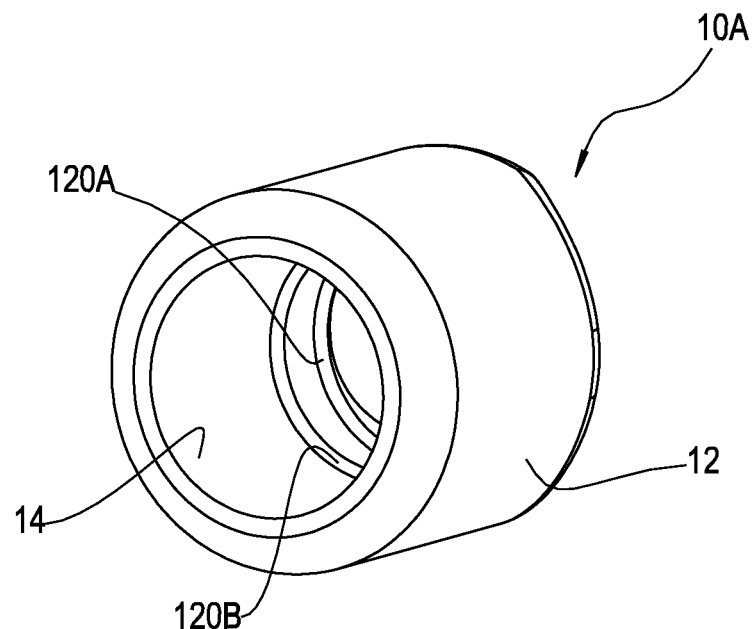
FIG. 14 is a rear perspective view of the alternative compression collar shown in FIG. 13.
Figure 15:
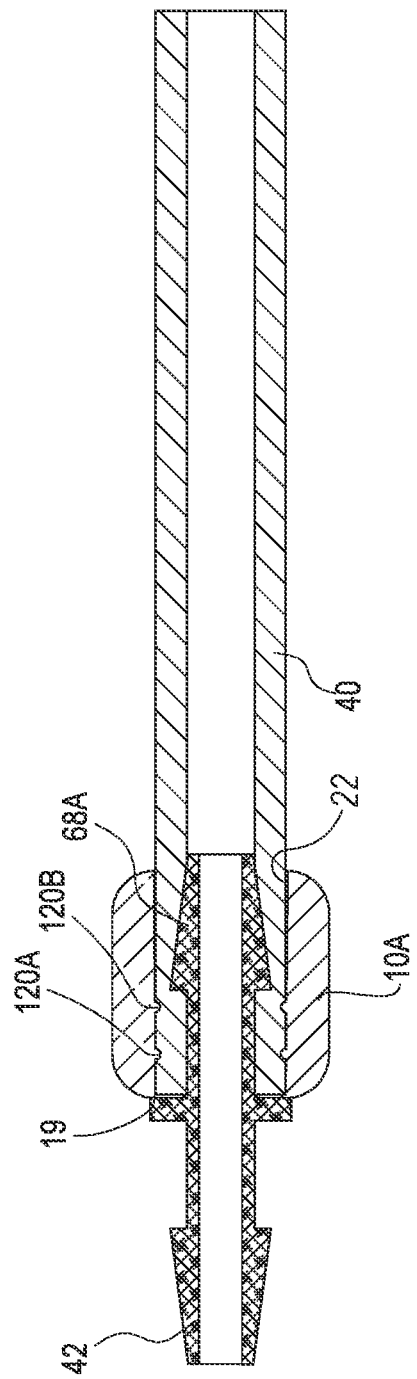
FIG. 15 is a cross sectional side view of the alternative compression collar shown in FIG. 13 coupled with the tube and the tube fitting.

Depicted in FIGS. 13 and 14 are perspective views of an alternative embodiment of a compression collar 10A incorporating features of the present invention. Like elements between compression collars 10 and 10A are identified by like reference characters. Compression collars 10 and 10A are identical except that compression collar 10A includes a pair of spaced apart compression ribs 120A and 120B disposed on interior surface 14 of tubular body 12 so as to radially inwardly project into throughway 22 and encircle throughway 22. Although not required, in the depicted embodiment compression ribs are annular, i.e., in the form of annular rings. Compression ribs 120A and 120B are typically disposed at or toward first end 18 of body 12 so that when tube fitting 42 and tube 40 are coupled together and disposed within throughway 22 of compression collar 10A, as shown in FIG. 15, compression ribs 120A and 120B are disposed between barb 68A and terminal end face 23 (FIG. 13) of compression collar 10A. That is, compression ribs 120A and 120B project into and compress tube 40 behind barb 68A so as to further secure tube 40 to tube fitting 42 and further enhance the liquid tight seal between tube 40 and tube fitting 42. In alternative embodiments, compression collar 10A can be formed with at least or less than 1, 2, 3, 4, or 5 spaced apart compression ribs or with a range between any two of the foregoing numbers.

Figure 16:
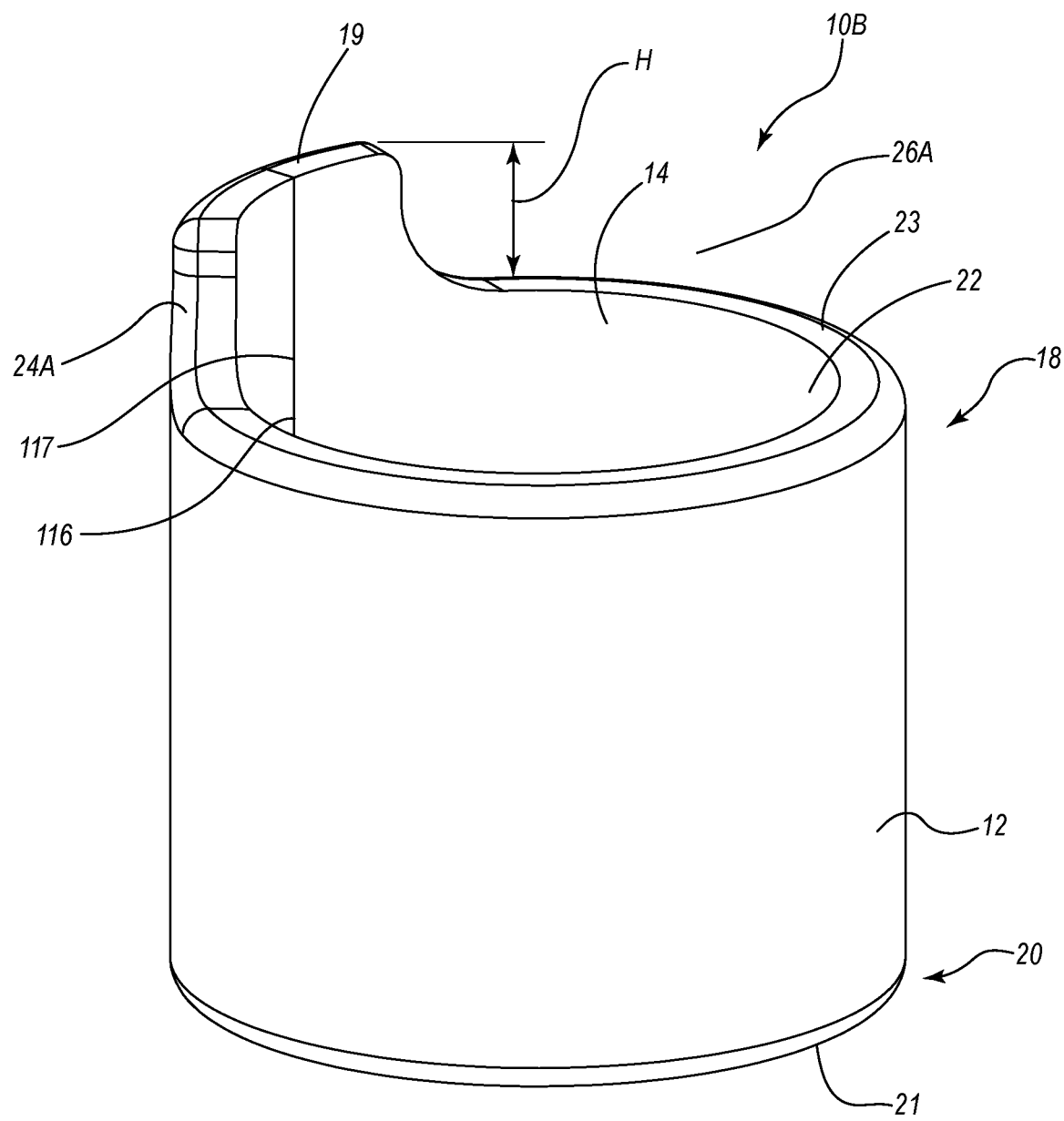
FIG. 16 is a perspective view of an alternative embodiment of a compression collar having a tubular body with a single spacer tab outwardly projecting therefrom.

Depicted in FIG. 16 is an alternative embodiment of a compression collar 10B. Like elements between compression collar 10 and 10B are identified by like reference characters. For example, compression collar 10B include tubular body 12 extending between terminal end face 23 at first end 18 and terminal end face 21 and second end 20. Tubular body 12 has interior surface 14 that bounds throughway 22 extending therethrough. However, in contrast to compression collar 10, compression collar 10B includes only a single spacer tab 24A outwardly projecting from first end 18 of tubular body 12. Single spacer tab 24A is shown projecting from terminal end face 23. In turn, only a single window 26A is formed. Window 26A is bounded on its opposing ends by the opposing ends of spacer tab 24A and is bounded on one side by the exposed area of terminal end face 23.

It is appreciated that spacer tab 24A can have a variety of different widths, i.e., the distance that spacer tab 24A extends along terminal end face 23. For example, with reference to the full annular length of terminal end face 23, spacer tab 24A can have a width that is at least or less than 5%, 10%, 15%, 20%, 30%, 40%, 50%, 60% of the full annular length of terminal end face 23 or is in a range between any two of the percent values. Spacer tab 24A also typically has a height H extending between terminal end face 23 and terminal end face 19 that is at least or less than 0.5 mm, 1 mm, 1.5 mm, 2 mm, 3 mm, 4 mm, 5 mm, 7 mm, 10 mm, 15 mm, 20 mm or is in a range between any of the two foregoing values. Height H can vary based on the diameter of tubular body 12. For example, in some embodiments the height H can increase as the diameter increases.

Although spacer tab 24A can be located at any location along terminal end face 23, in one embodiment spacer tab 24A can be positioned to increase the hoop strength of tubular body 12. For example, in one method of manufacture, as previously discussed, compression collar 10B can be produced by injection molding. In this method of manufacture, the production material is injected into a mold cavity having a substantially tubular, cylindrical configuration that corresponds to the desired shape of the compression collar. The material typically enters the cavity and flows in opposite directions around the cavity until the material meets up at an intersection location 116 to form a continuous loop. A weld line 117 can be formed where the material flows together and welds together but does not mix. Intersection location 116 and weld line 117 will typically extend along the length of compression collar 10B between terminal end faces 21 and 23. The material will often not fully blend or mix at intersection location 116/weld line 117, depending on the properties of the material, and thus will be weaker in lateral tension at intersection location 116/weld line 117. To help increase the tensile strength of compression collar 10B at intersection location 116/weld line 117 so that compression collar 10B does not fail as it is being radially expanded for attachment, spacer tab 24A can be formed at intersection location 116/weld line 117. That is, by positioning spacer tab 24A in alignment with intersection location 116/weld line 117, more material is disposed along intersection location 116/weld line 117, thereby increasing the tensile strength along intersection location 116/weld line 117 and increasing the overall hoop strength of compression collar 10B.

As a result of spacer tab 24A, there is typically less radial expansion of tubular body 12 at intersection location 116 during the expansion process than at the remainder of tubular body 12 where spacer tab 24A does not exist. Thus, to help ensure a more uniform expansion of tubular body 12, tubular body 12 will often only be made with one spacer tab 24A formed therein. However, as discussed below, multiple spacer tabs 24 can also be formed.

Figure 17A:
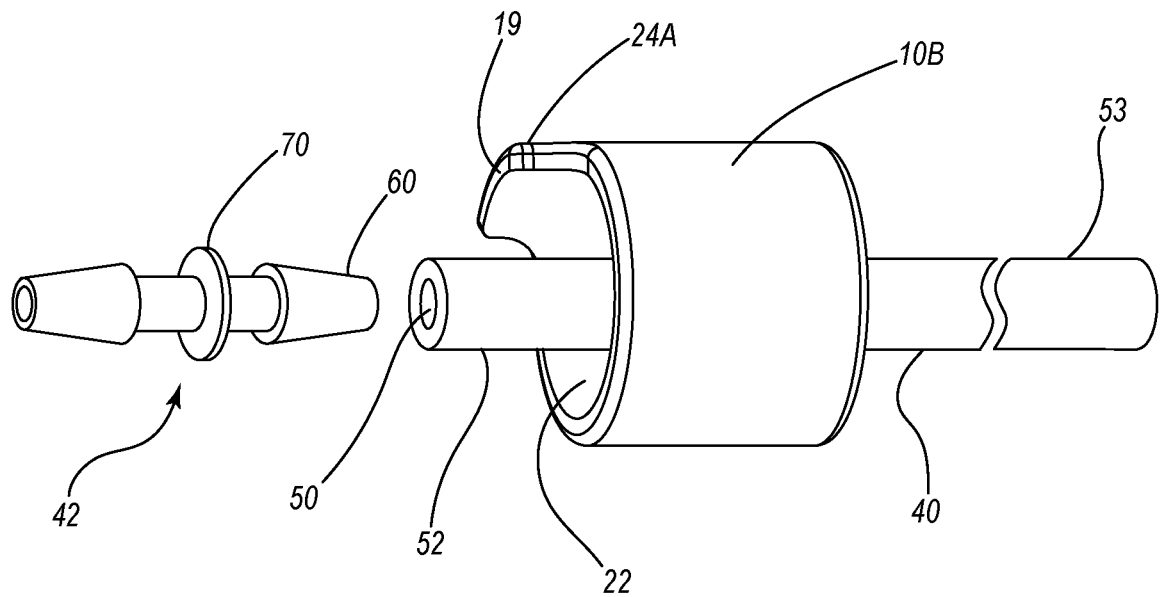
FIG. 17A is a perspective view of the compression collar shown in FIG. 16 in an expanded state and being coupled with a tube and tube fitting.
Figure 17B:
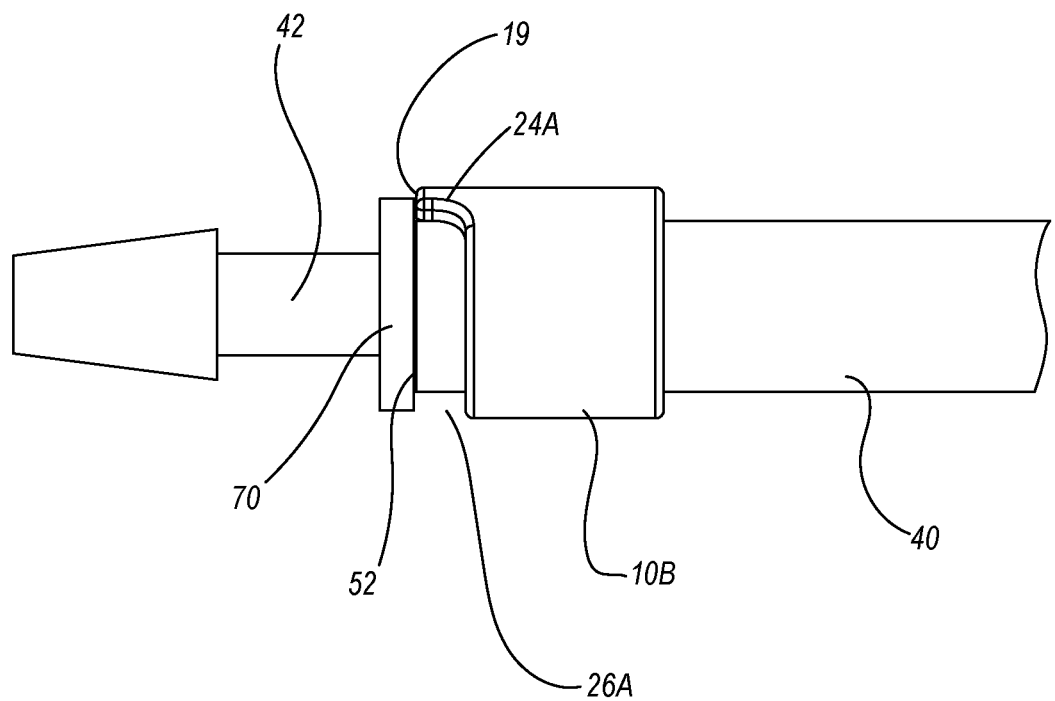
FIG. 17B is an elevated side view of the compression collar of FIG. 17A in a constricted state coupling the tube with the tube fitting.

Compression collar 10B is used in substantially the same way as previously discussed with regard to compression collar 10. For example, compression collar 10 is initially expanded in the same way as previously discussed with regard to compression collar 10. Turning to FIGS. 17A and 17B, once compression collar 10B is in the expanded state, first end 52 of tube 40 is advanced into throughway 22 of compression collar 10B. Because compression collar 10B does not include stop lips 32, tube 40 can be freely passed entirely through compression collar 10B, if desired.

Next, first end 60 of tube fitting 42 is advanced into passage 50 of tube 40 at first end 52 while tube 40 is partially disposed within throughway 20 of compression collar 10B. Tube fitting 42 is typically advanced into passage 50 prior to significant constricting of compression collar 10B so that compression collar 10B does not interfere with the insertion of tube fitting 42. Furthermore, tube 40 is typically sufficiently flexible that tube fitting 42 can be manually pressed into passage 50. In other embodiments, however, a tool or machine can be used to assist in the insertion of tube fitting 42.

Tube fitting 42 is advanced until flange 70 butts against the terminal end of tube 40. As needed, the assembled tube fitting 42 and tube 40 are moved so that terminal end 19 of spacer tab 24A butts against flange 70 of tube fitting 42. That is, tube fitting 42 and tube 40 can be assembled outside of compression collar 10B and then moved into place. Alternatively, tube 40 or tube fitting 42 can be held at the desired location relative to compression collar 10B while the other of tube 40 or tube fitting 42 is coupled thereto. In this method, no movement of tube 40 or tube fitting 42 is required relative to compression collar 10B once tube 40 and tube fitting 42 are coupled together. After tube fitting 42 and tube 40 are properly positioned, compression collar 10 is left to automatically, resiliently rebound back toward the constricted state. At a minimum, compression collar 10 resiliently rebounds so as to have an inner diameter that is smaller than the outer diameter of tube 40, thereby compressing tube 40. As compression collar 10 resiliently constricts, it radially inwardly pushes and constricts tube 40, so as to form a uniform, annular, liquid tight seal between tube 40 and barb 68A, in the same way as previously discussed and depicted with regard to FIG. 12.

Window 26A enables a visual inspection of first end 52 of tube 40 to ensure that first end 52 of tube 40 remains adjacent to or butted against flange 70 while compression collar 10B is positioned adjacent to or butted against flange 70, thereby ensuring that both tube 40 and tube fitting 42 are properly positioned within compression collar 10B so that compression collar 10B produces the desired liquid tight seal between tube 40 and tube fitting 42.

Depending on the situation, variations in the assembly process may also be used. For example, if tube 40 has a free second end 53 that is opposite first end 52, tube 40 and tube fitting 42 could be coupled together outside of compression collar 10B. Once assembled, second end 53 could be advanced through throughway 22 of compression collar 10B until spacer tab 24A butts against flange 70 of tube fitting 42. In yet another alternative, compression collar 10B may be configured so that in the expanded state, tube fitting 42 (including flange 70) can pass entirely through throughway 22. In this embodiment, tube 40 and tube fitting 42 could again be coupled together outside of compression collar 10B. Once assembled, tube fitting 42 having tube 40 therein could be advanced through compression collar 10 until the side face of flange 70 is aligned with terminal end face 19 of spacer tab 24A. The assembly could then be held in this position until compression collar 10B sufficiently constricts so that spacer tab 24A butts against flange 70. Other methods of assembly can also be used depending on the facts.

Figure 18:
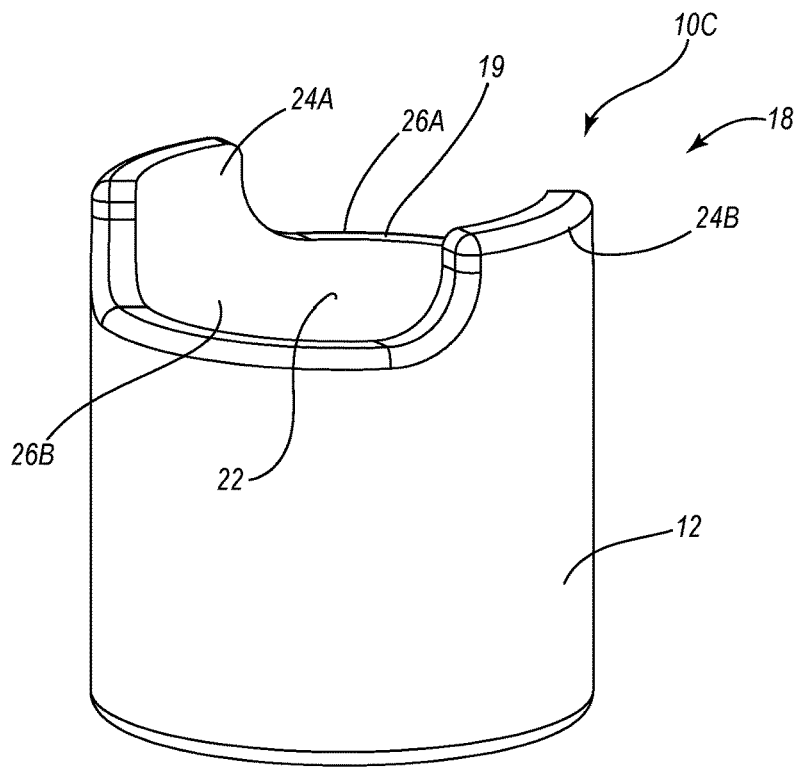
FIG. 18 is an alternative embodiment of the compression collar shown in FIG. 16 have two spacer tabs projecting from the tubular body.

In an alternative embodiment, it is appreciated that compression collar 10B can be formed with 2, 3, 4, or more spaced apart spacer tabs 24. For example, depicted in FIG. 18 is a compression collar 10C. Compression collar 10C has the same structural elements and is used in the same way as compression collar 10B except that compression collar 10C includes a second spacer tab 24B projecting from first end 18 of tubular body 12. Again, spacer tabs 24A and 24B are shown projecting from terminal end face 23 and bound windows 26A and 26B therebetween. Spacer tabs 24A and 24B are opposingly facing and are disposed on opposing sides of terminal end face 23. Other spacings of spacer tabs 24A and 24B can also be used.

Figure 19:
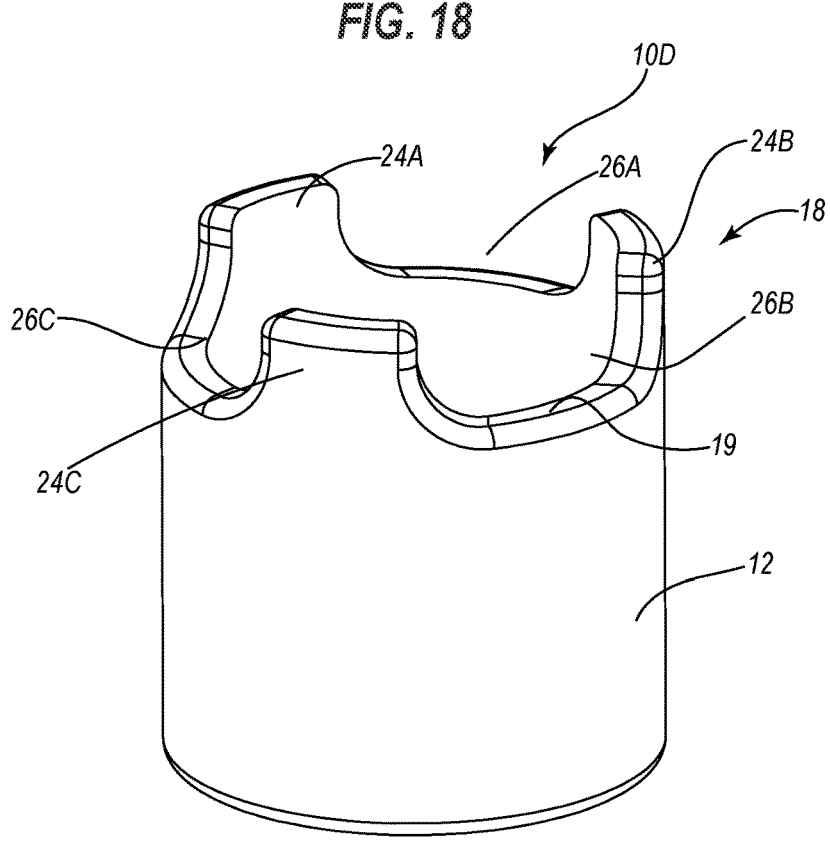
FIG. 19 is a perspective view of an alternative embodiment of the compression collar shown in FIG. 18 having three spacer tabs projecting from the tubular body.

In another alternative embodiment depicted in FIG. 19, a compression collar 10D is provided. Compression collar 10D has the same structural elements and is used in the same way as compression collars 10B and 10C except that compression collar 10D also includes a third spacer tab 24C longitudinally projecting from first end 18 of tubular body 12. Again, spacer tabs 24A, 24B, and 24C are shown projecting from terminal end face 23 and bound windows 26A, 26B, and 26C therebetween.

Figure 20:
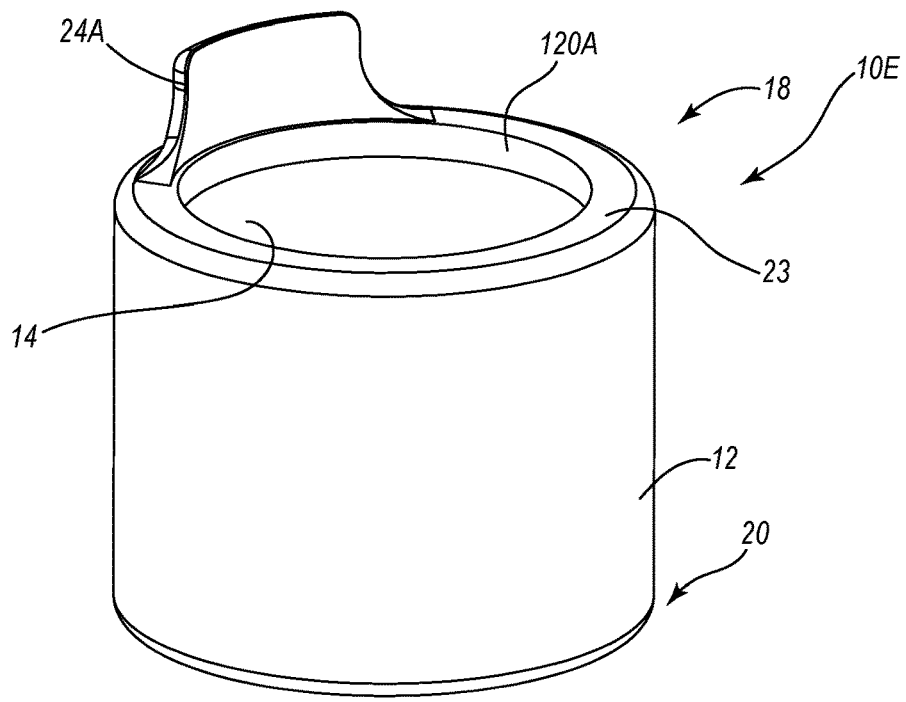
FIG. 20 is a perspective view of an alternative embodiment of the compression collar shown in FIG. 16 where the compression collar further includes a single annular compression rib radially inwardly projecting from the tubular body.
Figure 21:
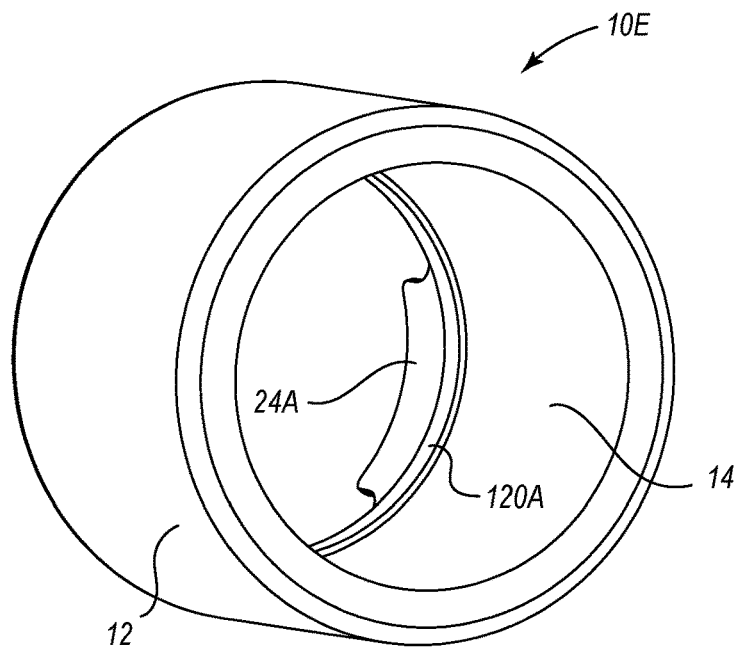
FIG. 21 is a bottom perspective view of the compression collar shown in FIG. 20.

Depicted in FIGS. 20 and 21 is another alternative embodiment of a compression collar 10E that has the same structural elements and can be used in the same way as compression collars 10B-10D. Compression collar 10E is distinguished from compression collar 10B by having annular compression rib 120A inwardly projecting from interior surface 14 at first end 18. In the depicted embodiment, compression rib 120A is shown being flush with terminal end face 23. In other embodiments, compression rib 120A can be spaced apart from terminal end face 23 and located more toward second end 20.

Figure 22:
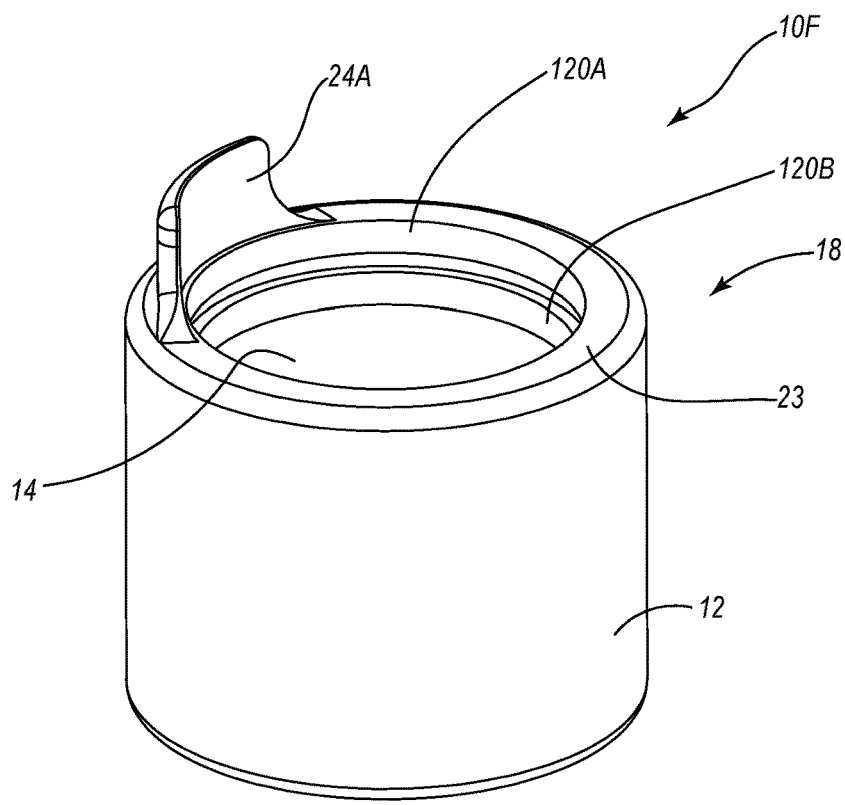
FIG. 22 is a perspective view of an alternative embodiment of the compression collar shown in FIG. 20 having a second annular compression rib radially inwardly projecting from the tubular body.

Compression rib 120A is positioned and designed to function in the same way as previously discussed with regard to compression collar 10A when discussing FIGS. 13-15. Specifically, compression rib 120A is positioned so that when tube fitting 42 and tube 40 are coupled together and disposed within throughway 22 of compression collar 10E, compression rib 120A is disposed between barb 68A (FIG. 15) and terminal end face 23 of compression collar 10E or at terminal end face 23. Compression rib 120A projects into and compresses tube 40 behind barb 68A so as to further secure tube 40 to tube fitting 42 and further enhance the liquid tight seal between tube 40 and tube fitting 42. In alternative embodiments, compression collar 10E can be formed with at least or less than 2, 3, 4, or 5 spaced apart compression ribs or with a range between any two of the foregoing numbers. For example, depicted in FIG. 22 is another alternative embedment of a compression collar 10F that has the same structural elements and can be used in the same way as compression collar 10E except that compression collar 10F also includes second compression rib 120B. Second compression rib 120B also radially inwardly projects from interior surface 14 and is located at first end 18 of tubular body 12 but is spaced apart from first compression rib 120A. Second compression rib 120B functions the same way as first compression rib 120A.

Figure 23:
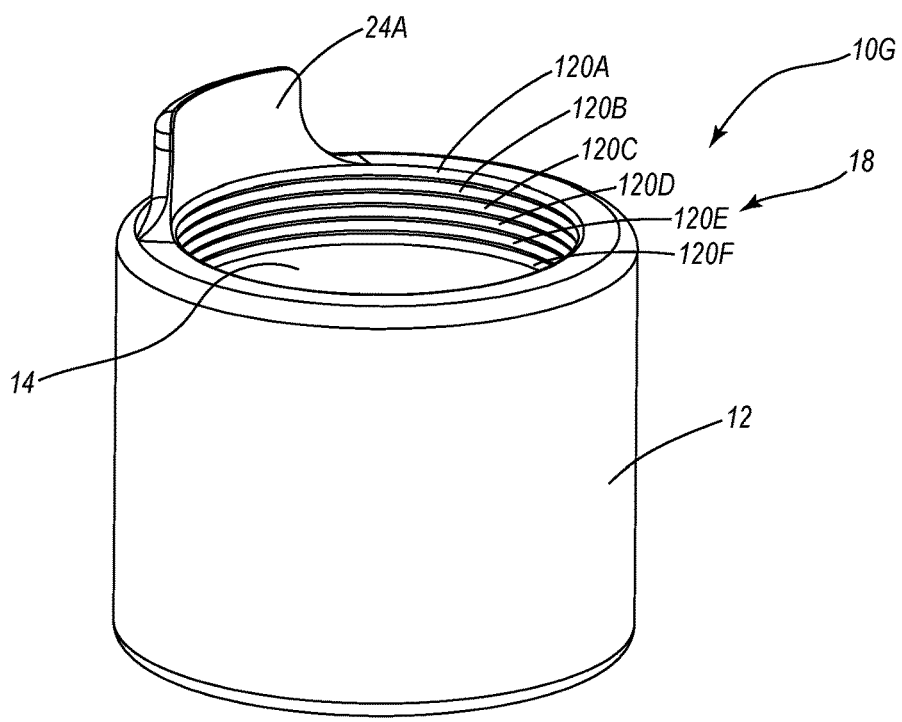
FIG. 23 is a perspective view of an alternative embodiment of the compression collar shown in FIG. 22 having six annular compression ribs radially inwardly projecting from the interior surface of the tubular body.

FIG. 23 shows an alternative embodiment of a compression collar 10G that has the same structural elements and can be used in the same way as compression collar 10E. However, compression collar 10G has a plurality of compression ribs 120A-120F that radially inwardly project from interior surface 14 of tubular body 12 at first end 18. Compression ribs 120A-120F can each be directly adjacently disposed or can be spaced apart. Again, compression ribs 120A-120F project into and compress tube 40 behind barb 68A so as to further secure tube 40 to tube fitting 42 and further enhance the liquid tight seal between tube 40 and tube fitting 42.

Figure 24:
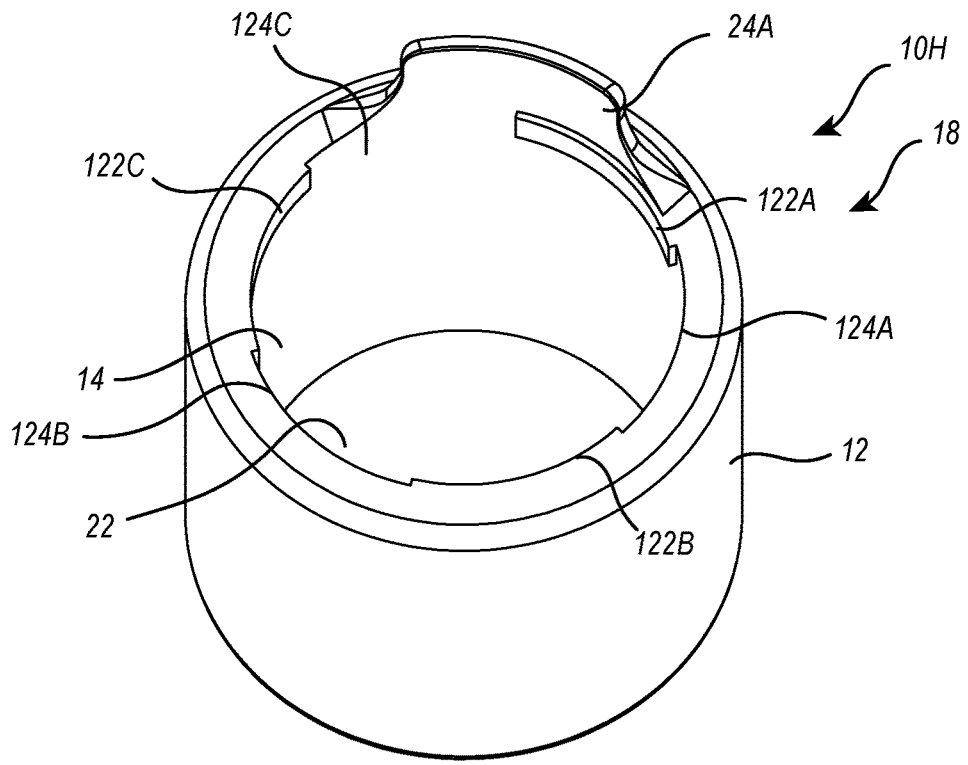
FIG. 24 is a perspective view of another alternative embodiment of the compression collar shown in FIG. 16 where the compression collar further includes a plurality of radially spaced apart compression ribs radially inwardly projecting from the interior surface of the body.

Depicted in FIG. 24 is another alternative embodiment of a compression collar 10H that has the same structural elements and can be used in the same way as compression collar 10E. In the embodiments of compression collars 10E-10G, compression ribs 120 are shown as being annular, i.e., annular rings. In contrast, compression collar 10H includes compression ribs 122A-122C that radially inwardly project from interior surface 14 of body 12 at first end 18 but are not annular. Rather, compression ribs 122A-122C are radially spaced apart and are separated by gaps 124A-124C. In the depicted embodiment, compression ribs 122A-122C are disposed at the same location along the length of tubular body 12. That is, compression ribs 122A-122C are disposed within a common plane that orthogonally passes through longitudinal axis 25 (FIG. 4) of tubular body 12. In an alternative embodiment, compression ribs 122A-122C can be staggered along the length of tubular body 12 at first end 18.

In the depicted embodiment, three non-annular compression ribs 122A-122C are shown. In alternative embodiments, 1, 2, 4, or more non-annular compression ribs 122 can be used. As with compression ribs 120, compression ribs 122 project into and compress tube 40 behind barb 68A so as to further secure tube 40 to tube fitting 42 and further enhance the liquid tight seal between tube 40 and tube fitting 42.

One potential concern with using annular compression ribs 120 is that during the expansion process, prongs 98 from expansion mechanism 90 (FIG. 8B) could press against and potentially deform or damage that annular compression ribs 120 so that they no longer properly function to seal tube 40 to tube fitting 42. By using non-annular, spaced apart compression ribs 122, expansion mechanism 90 (FIG. 8B) can be designed with prongs 98 that sit only within gaps 124 and do not sit directly against compression ribs 122. Accordingly, as compression collar 10H is expanded by prongs 98, there is no risk of compression ribs 122 being deformed or damaged by prongs 98.

Figure 25:
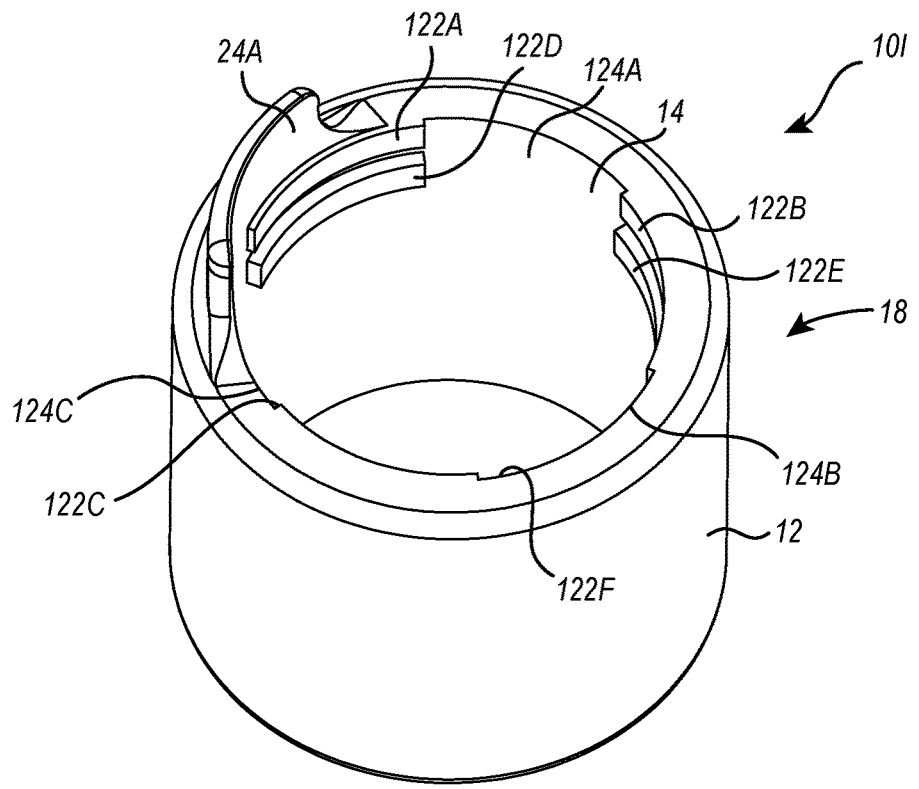
FIG. 25 is a perspective view of an alternative embodiment of the compression collar shown in FIG. 24 including a second set of radially spaced apart compression ribs that are disposed at a second distance along the length of the tubular body.

Depicted in FIG. 25 is a further alternative embodiment of a compression collar 10I that has the same structural elements and can be used in the same way as compression collar 10H. Compression collar 10I is the same as compression collar 10H except that compression collar 10I includes a second row of compression ribs 122D-122F. Compression ribs 122D-122F can have the same configuration and function as compression ribs 122A-122C and be spaced apart by gaps 124A-124C. Furthermore, compression ribs 122D-122F can have the same alternatives as compression ribs 122A-122C. However, compression ribs 122D-122F are placed at a different location along the length of tubular body 12.

Figure 26:
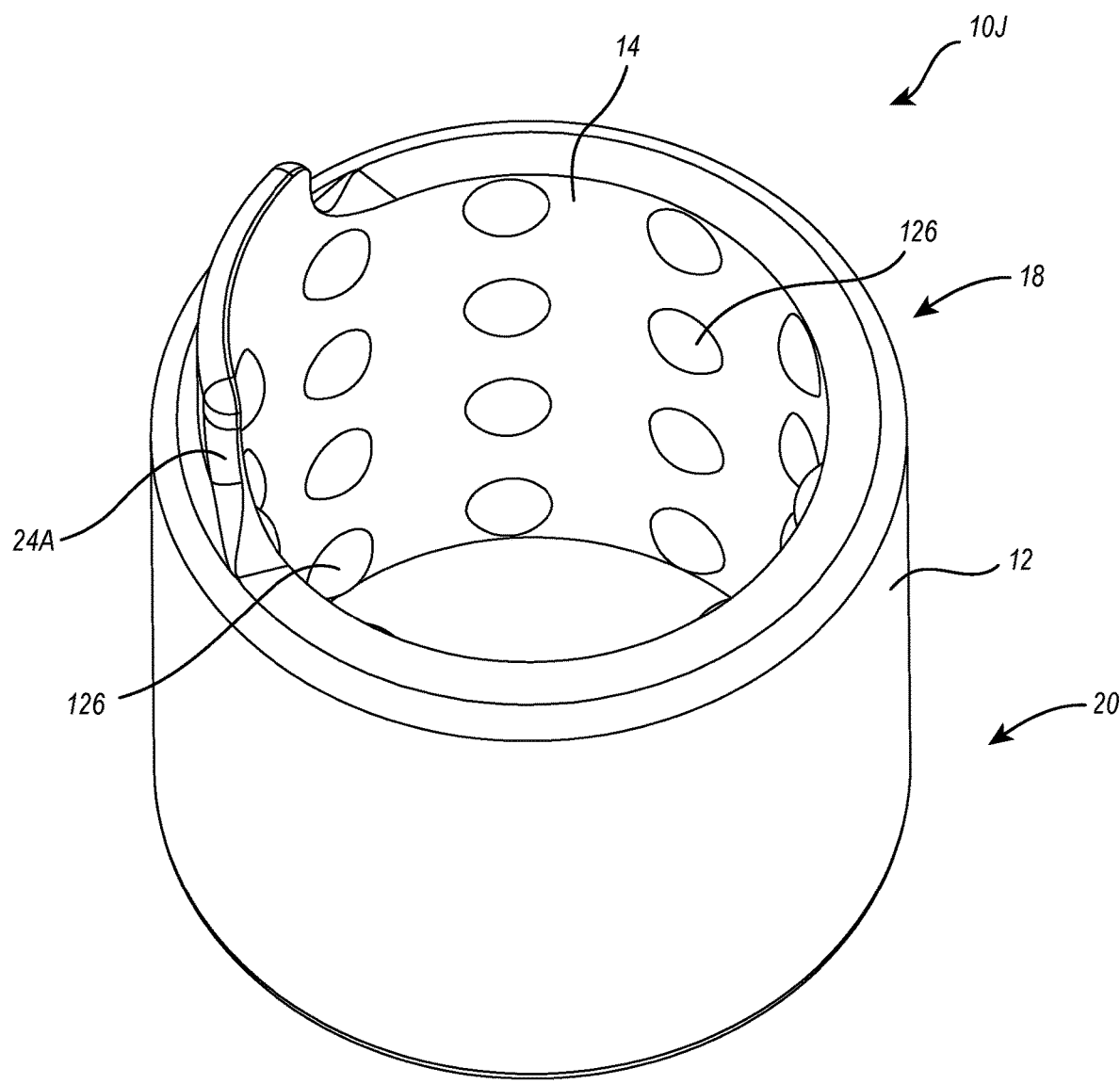
FIG. 26 is a perspective view of an alternative embodiment of the compression collar shown in FIG. 16 comprising a plurality of spaced apart compression ribs disposed over the entire interior surface of the tubular body.

In the above discussed embodiments, compression ribs 122 are depicted as linear and are located at first end 18. In alternative embodiment, however, the compression ribs need not be linear and can also be located at second end 20. For example, depicted in FIG. 26 is a compression collar 10J having a plurality of compression ribs 126 radially inwardly projecting from interior surface 14. However, compression ribs 126 are spaced apart over the entire interior surface 14 between first end 18 and second end 20. Furthermore, compression ribs 126 are shown as being circular. However, in other embodiments, compression ribs could be oval, elliptical, square, irregular or have other polygonal configurations. Compression ribs 126 still function to project into and compress tube 40 so as to further secure tube 40 to tube fitting 42 and further enhance the liquid tight seal between tube 40 and tube fitting 42.

Figure 27:
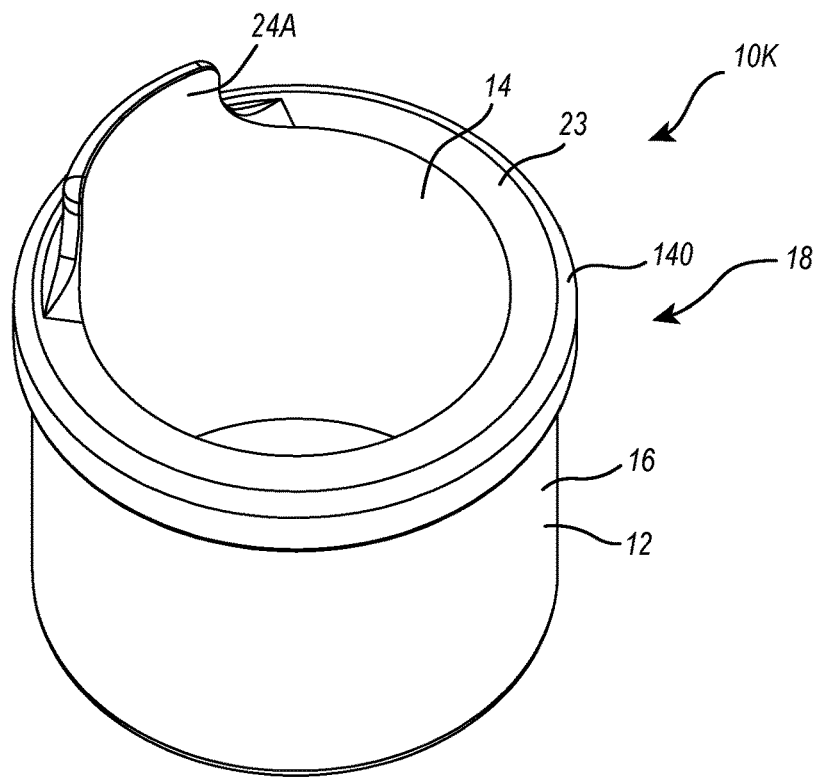
FIG. 27 is a perspective view of an alternative embodiment of the compression collar shown in FIG. 16 where the compression collar further includes a retention rib radially outwardly projecting from the exterior surface of the tubular body.
Figure 28:
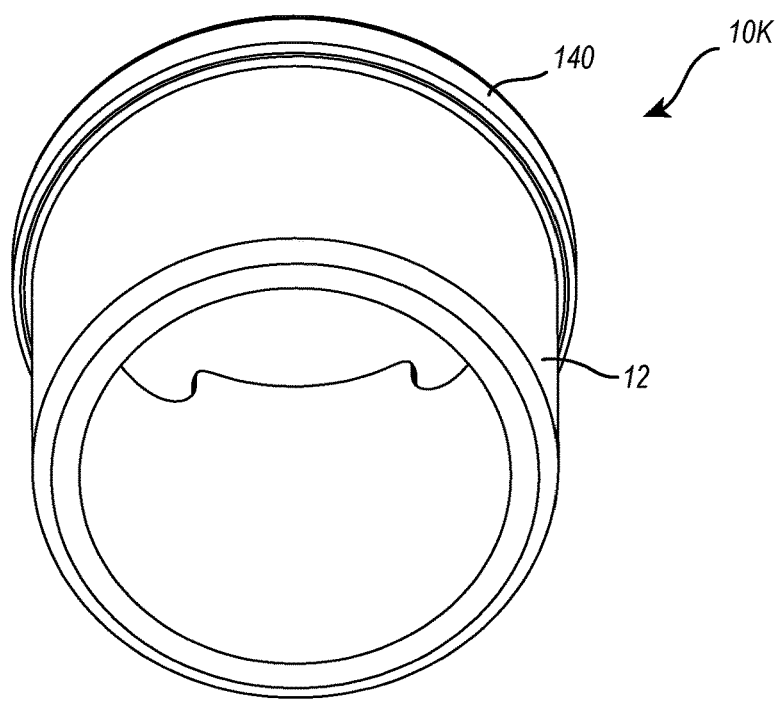
FIG. 28 is a bottom perspective view of the compression collar shown in FIG. 27.

In another alternative embodiment depicted in FIGS. 27 and 28, a compression collar 10K is provided. Compression collar 10K has the same structural elements and is used in the same way as compression collar 10B. The distinction between compression collar 10K and compression collar 10B is that compression collar 10K has a retention rib 140A that radially outwardly projects from exterior surface 16 of tubular body 12 at first end 18. Retention rib 140A is depicted as being annular and flush with terminal end face 23. However, in alternative embodiments, retention rib 140A can be located at other locations along the length of tubular body 12, i.e., spaced apart from terminal end face 23, and need not be annular. For example, retention rib 140A could comprise a plurality of spaced apart non-annular retention ribs, i.e., 2, 3, 4, or more retention ribs, such as compression ribs 122.

Figure 29:
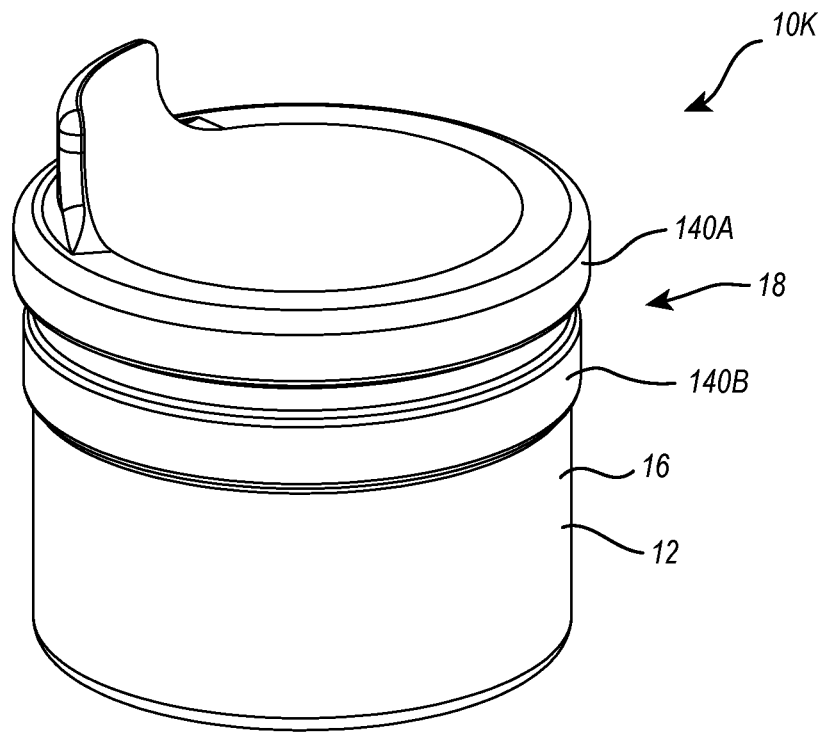
FIG. 29 is a perspective view of an alternative embodiment of the compression collar shown in FIG. 27 that further includes a second retention rib outwardly projecting from the first end of the tubular body.
Figure 30:
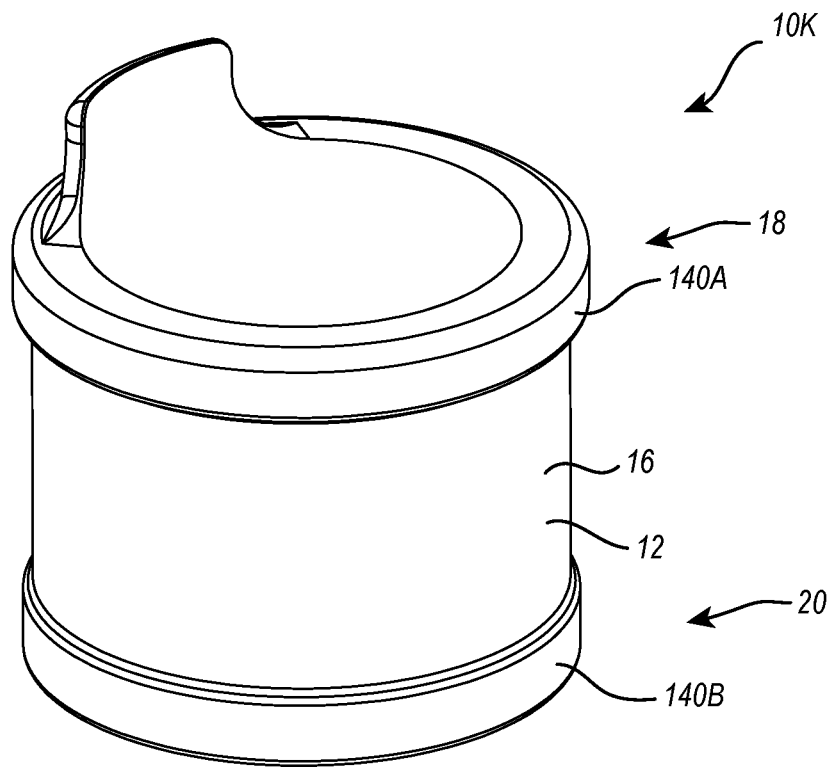
FIG. 30 is a perspective view of an alternative embodiment of the compression collar shown in FIG. 29 wherein the second retention rib is disposed at a second end of the tubular body.

In contrast to compression ribs 120 and 122 that project into and directly compress tube 40, retention rib 140A reinforces first end 18 of tubular body 12. This reinforcement helps to ensure that first end 18 fully constricts after expansion and thereby helps to ensure that compression collar 10K compresses tube 40 to secure tube 40 to tube fitting 42 and further ensures the liquid tight seal between tube 40 and tube fitting 42. If desired, more than one retention rib 140 can be formed on tubular body 12. For example, in FIG. 29 compression collar 10K includes a second retention rib 140B radially outwardly projecting from exterior surface at first end 18. Retention rib 140B can have the same alternatives as retention rib 140A. As desired, 3, 4 or more retention ribs 140 can be used. Furthermore, as depicted in FIG. 30, retention rib 140B or other retention ribs can also be disposed as second end 20. Even when located at second end 20, retention ribs 140 help ensure proper constriction of tubular body 12 for compressing tube 40.

Figure 31:
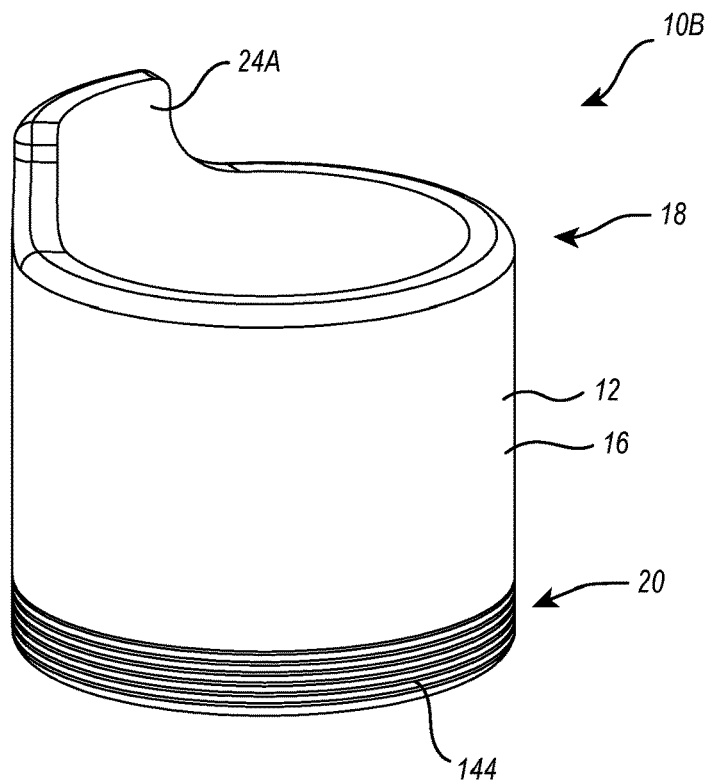
FIG. 31 is a perspective view of an alternative embodiment of the compression collar shown in FIG. 16 which includes gripping formed on the exterior surface of the tubular body.

Depicted in FIG. 31 is compression collar 10B as previously discussed above with regard to FIG. 16. However, compression collar 10B has now been modified to include gripping 144 formed on exterior surface 16. Gripping 144 can be in the form of linear ribs or any other shape of projections that will assist a using in gripping and moving compression collar 10B. For example, gripping can be the same shape as compression ribs discussed with regard to FIG. 26. Although gripping 144 is shown disposed at second end 20, it can also be disposed at first end 10 or can be disposed in patterns or at spaced apart locations over the entirety of exterior surface 16.

Figure 32:
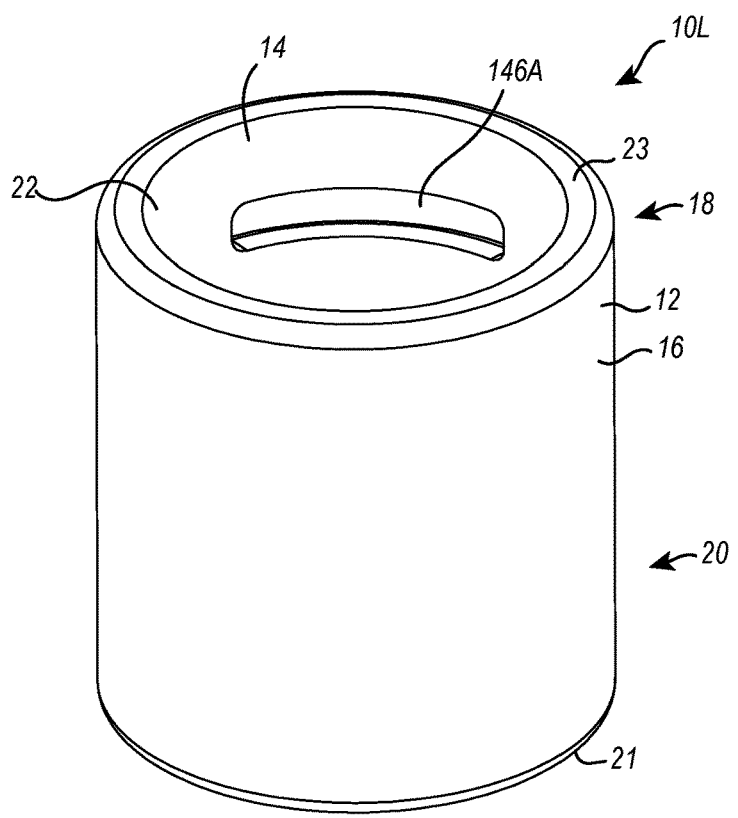
FIG. 32 is a perspective view of an alternative embodiment of a compression collar having a single window extending through the tubular body.

Depicted in FIG. 32 is another alternative embodiment of a compression collar 10L. Like elements between compression collar 10L and other the compression collars disclosed herein are identified by like reference characters. Specifically, compression collar 10L includes tubular body 12 extending between terminal end face 23 at first end 18 and terminal end face 21 and second end 20. Tubular body 12 has interior surface 14 that bound throughway 22 and also has exterior surface 16. Compression collar 10L is distinguished from compression collar 10B in the compression collar 10L does not include spacer tab 24A. Furthermore, compression collar 10L includes a window 146A that extends through tubular body 12 between interior surface 14 an exterior surface 16 at first end 18. Window 146A is spaced apart from terminal end face 23 so that window 146a is completely encircled by tubular body 12. In the depicted embodiment, window 146A is in the form of an elongated slot that extends partially around the circumference of tubular body 12. However, in other embodiments, window 146A can be in the form of a circle, ellipse, or other polygonal configurations.

Figure 33:
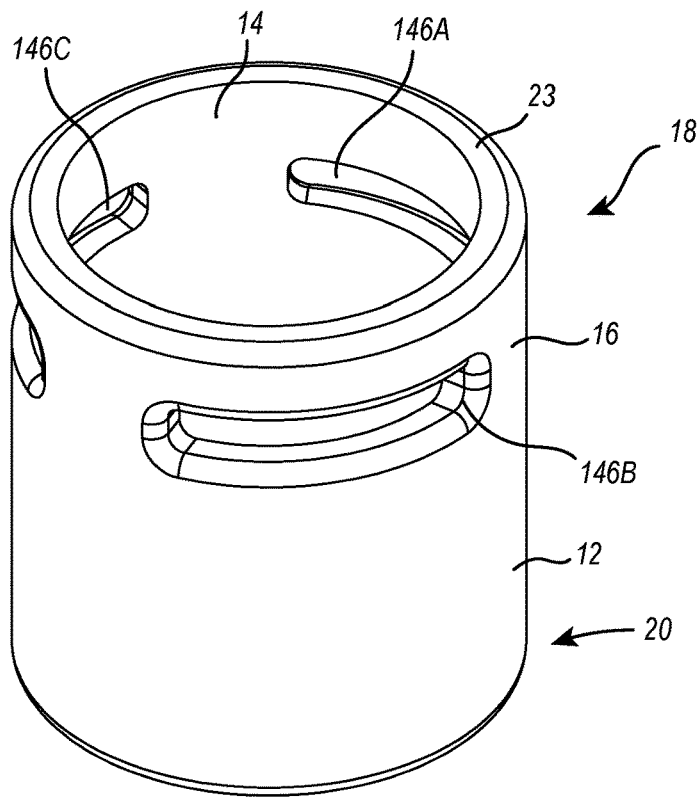
FIG. 33 is a perspective view of an alternative embodiment of the compression collar shown in FIG. 32 where the compression collar has three radially spaced apart windows extending through the tubular body.

Compression collar 10L functions the same and is used in the same way as compression collar 10B, previously discussed, except that once tube 40 and tube fitting 42 are coupled together, terminal end face 23 is butted directly against flange 70 of tube fitting 42. Window 146A can then be used to ensure that tube 40 is properly positioned within compression collar 10L. It is appreciated that any desired number of windows 146 can be used and that windows 146 can be disposed at a variety of different locations. For example, in contrast to having a single window 146A, it is appreciated that 2, 3, 4, or more windows can be disposed extending through tubular body 12 at the same location along the length of tubular body 12. FIG. 33 shows such an example where a plurality, more specifically three, of windows 146A, 146B, and 146C are spaced apart and extend through tubular body 12 at the same location along the length of tubular body 12. Again, windows 146 can be used to ascertain the position of tube 40.

Figure 34:
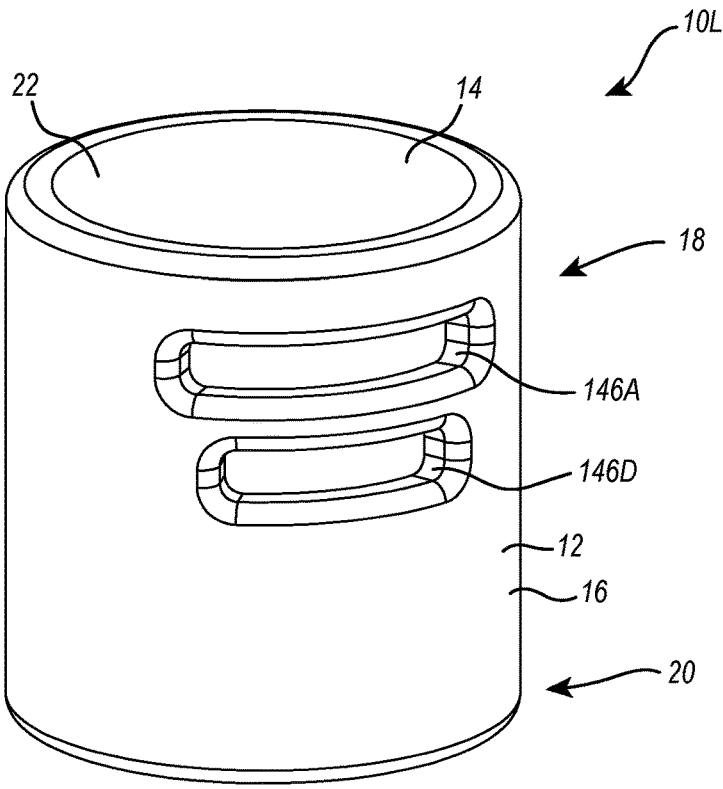
FIG. 34 is a perspective view of an alternative embodiment of the compression collar shown in FIG. 32 where the compression collar a second window extending through the tubular body that is longitudinally spaced apart from the first window.
Figure 35:
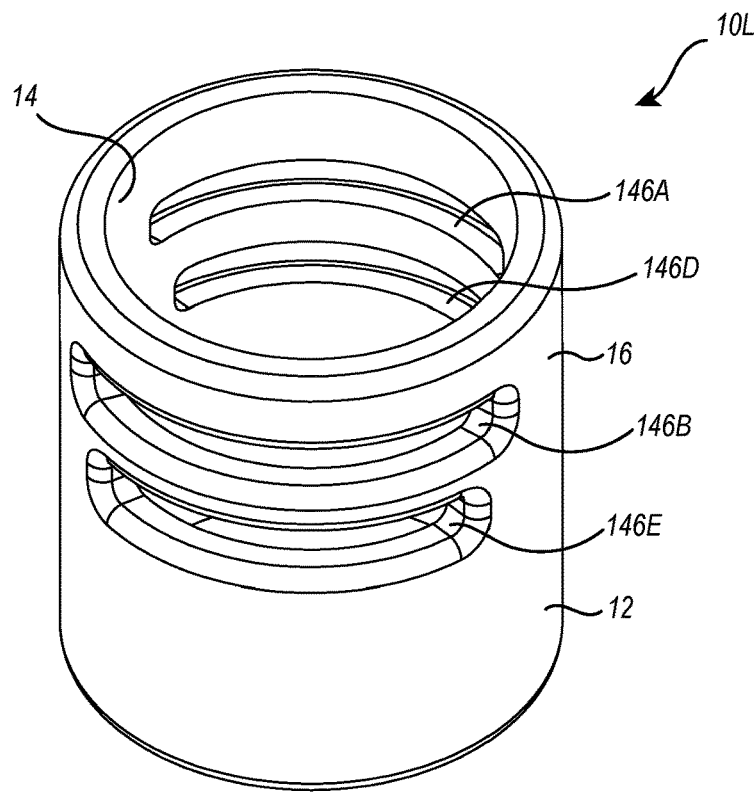
FIG. 35 is a perspective view of an alternative embodiment of the compression collar shown in FIG. 34 where the compression collar has two pairs of windows that are spaced apart along the longitudinally length of the tubular body.
Figure 36:
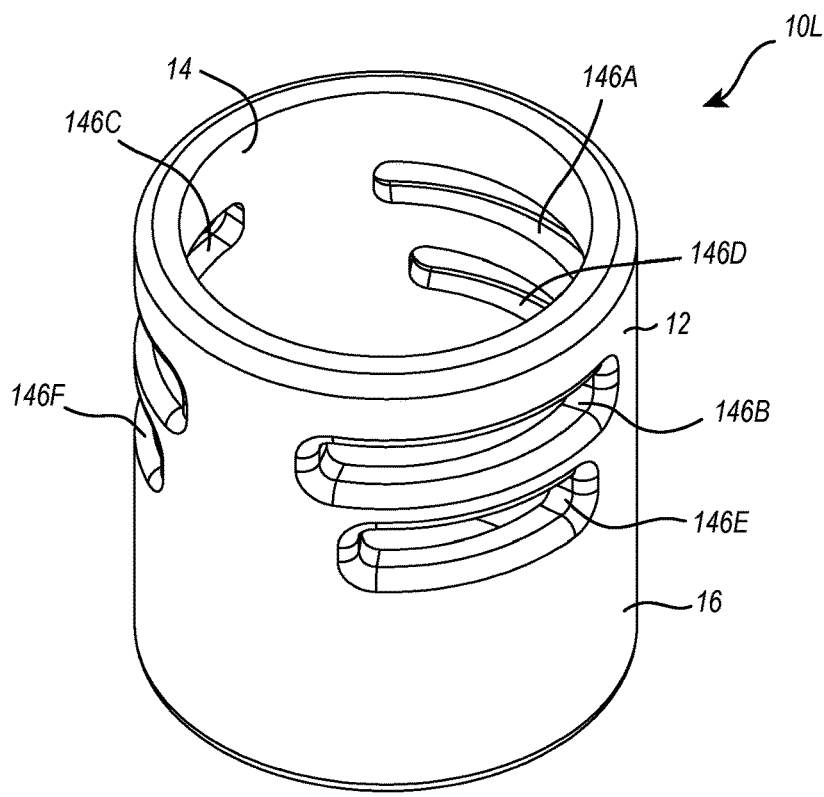
FIG. 36 is a perspective view of the compression collar shown in FIG. 35 where the compression collar has three sets of windows that are spaced apart radially and along the length of the tubular body.

In contrast to windows 146 being disposed at the same location along the length of tubular body 12, windows 146 can also be spaced apart along the length of tubular body 12. For example, in FIG. 34 compression collar 10L includes first window 146A and a second window 146D extending through tubular body 12 so as to be completely encircled by tubular body 12. However, windows 146A and 146D extend through tubular body 12 at two spaced apart locations along the length tubular body 12. FIG. 35 show an embodiment of compression collar 10L which shows a combination of the windows shown in FIGS. 33 and 34. Specifically, compression collar 10L has a first set of a plurality of windows, i.e., windows 146A and 146B, that are at a defined location along the length of tubular body 12 and a second set of a plurality of windows, i.e., windows 146D and 146E, that are located at a second location along the length of tubular body 12. FIG. 36 shows the same embodiment of compression collar 10L shown in FIG. 35 except that the first set of a plurality of windows includes three separate windows, i.e., windows 146A, 146B and 146C, while the second set of a plurality of windows includes three windows, i.e., windows 146D, 146E, and 146F. As needed, any desired number of windows can be used at any desired location.

Figure 37:
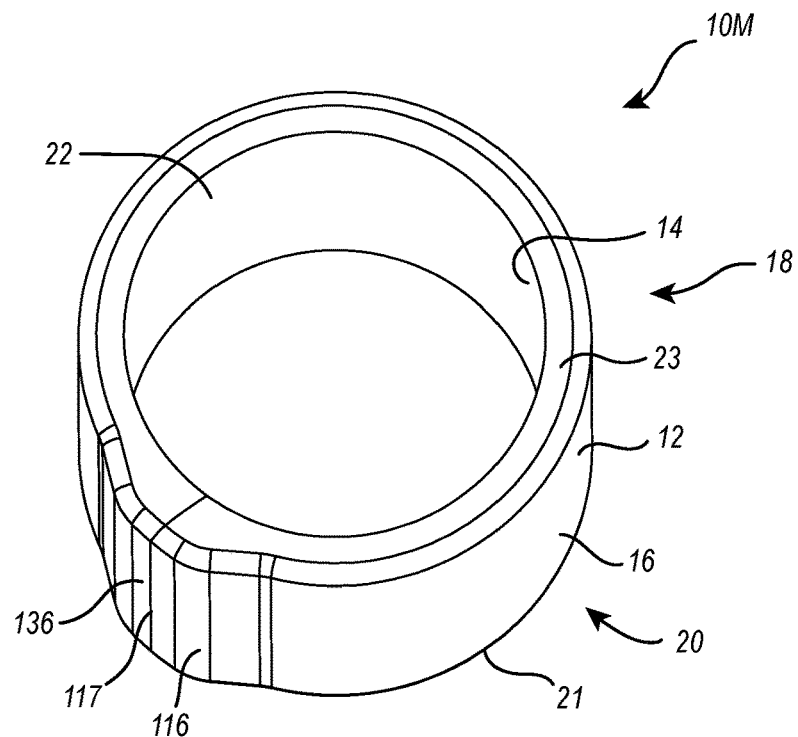
FIG. 37 is a perspective view of an alternative embodiment of a compression collar having a hump formed on the exterior surface of the tubular body.

Depicted in FIG. 37 is an alternative embodiment of a compression collar 10M that can achieve the same function and be used in the same way as the prior compression collars disclosed herein. Like elements between compression collar 10M and compression collar 10B are identified by like reference characters. Compression collar 10M includes tubular body 12 that extends between terminal end face 23 and terminal end face 21 and that bounds throughway 22. As previously discussed with regard to compression collar 10B, compression collar 10M includes an intersection zone 116 that longitudinally extends between terminal end faces 23 and 21 and is where, during the injection molding process, the material used to form compression collar 10M flows together to form a continuous loop. Weld line 117 can be formed at intersection zone 116 where the material flows together and welds together. As also previously discussed, the material at intersection zone 116 will typically not uniformly blend or mix together so that the lateral tensile strength of the compression collar at intersection zone 116/weld line 117 is typically less than at other locations around the compression collar.

To compensate for this structural weakness, compression collar 10M is formed having an increased thickness at intersection zone 116. This increased thickness will typically longitudinally extend between first end 18 and second end 20. More specifically, a hump 136 is formed on exterior surface 16 of tubular body 12 along intersection zone 116/weld line 117 that extends between first end 18 and second end 20 and will typically extend between terminal end faces 23 and 21. Hump 136 is integrally formed with tubular body 12 as part of the molding process so that hump 136 and tubular body 12 form a single, continuous, unitary structure. As a result of hump 136, the overall hoop strength of compression collar is increased. In contrast to forming a single continuous hump, in alternative embodiments, two, three, or more spaced apart humps 136 could be formed along intersection zone 116.

Figure 38:
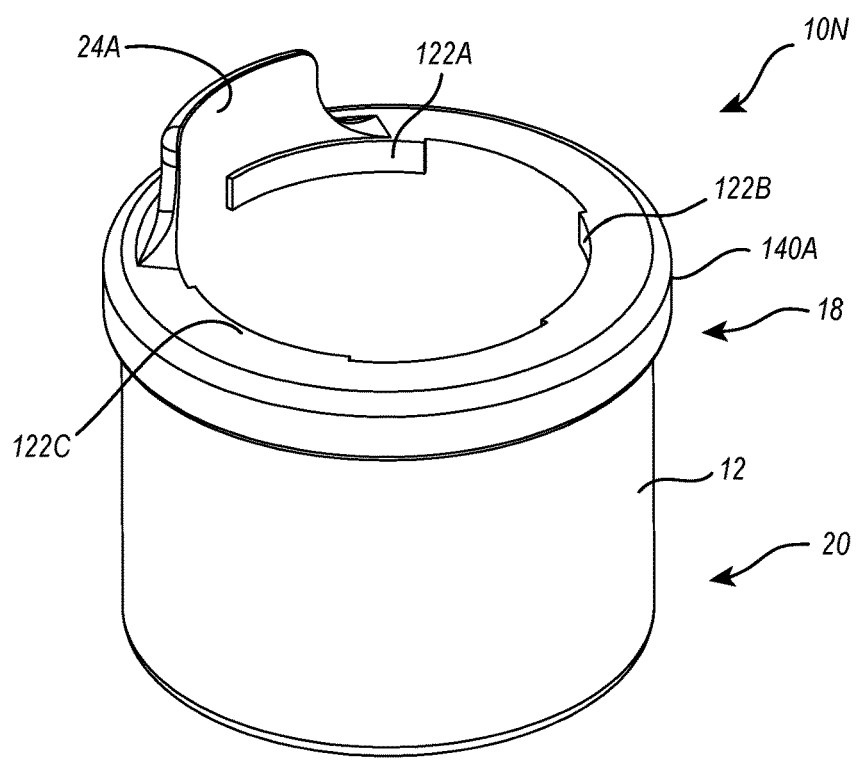
FIG. 38 is a perspective view of an alternative embodiment of a compression collar that includes a spacer tab, radially spaced apart compression ribs, and a annular retention rib.

In the foregoing alternative embodiments of compression collars, it is appreciated that the inventive compression collars can be formed with a variety of different features and that each feature achieves an independent unique benefit or improvement. In other alternative embodiments, it is appreciated that each of the independent features previously discussed can be mixed and matched into any desired combination. For example, alternative compression collars can be formed that include tubular body 12 and that can further include zero or one or more spacer tabs 24, zero or one or more stop lips 32, zero or one or more annular compression ribs 120, zero or one or more non-annular compression ribs 124 and/or 126, zero or one or more retention ribs 140, zero or one or more gripping 144, zero or one or more windows 26 and/or 146, and/or zero or one or more humps 136. By way of example and not by limitation, depicted in FIG. 38 is an alternative embodiment of a compression collar ION that includes tubular body 12 having spacer tab 24A, compression ribs 122A-122C and retention rib 140 formed thereon. Again, compression collars can also be formed having tublar body 12 and any combination of the above described features or alternatives of the above described features.

As previously discussed with regard to FIGS. 7-8B, expander 80 can be used to selectively expand compression collars 10. In the previously discussed method for expansion, a single expander 80 is inserted into one end of a compression collar 10 for expansion of the compression collar. In one alternative method of expansion, dual expanders 80 can be inserted into the opposing ends of a compression collar 10 to simultaneously expand the compression collar 10 at both opposing ends. This method can be helpful in retaining interior surface 14 more circular as compression collar 10 is expanded.

Figure 39:
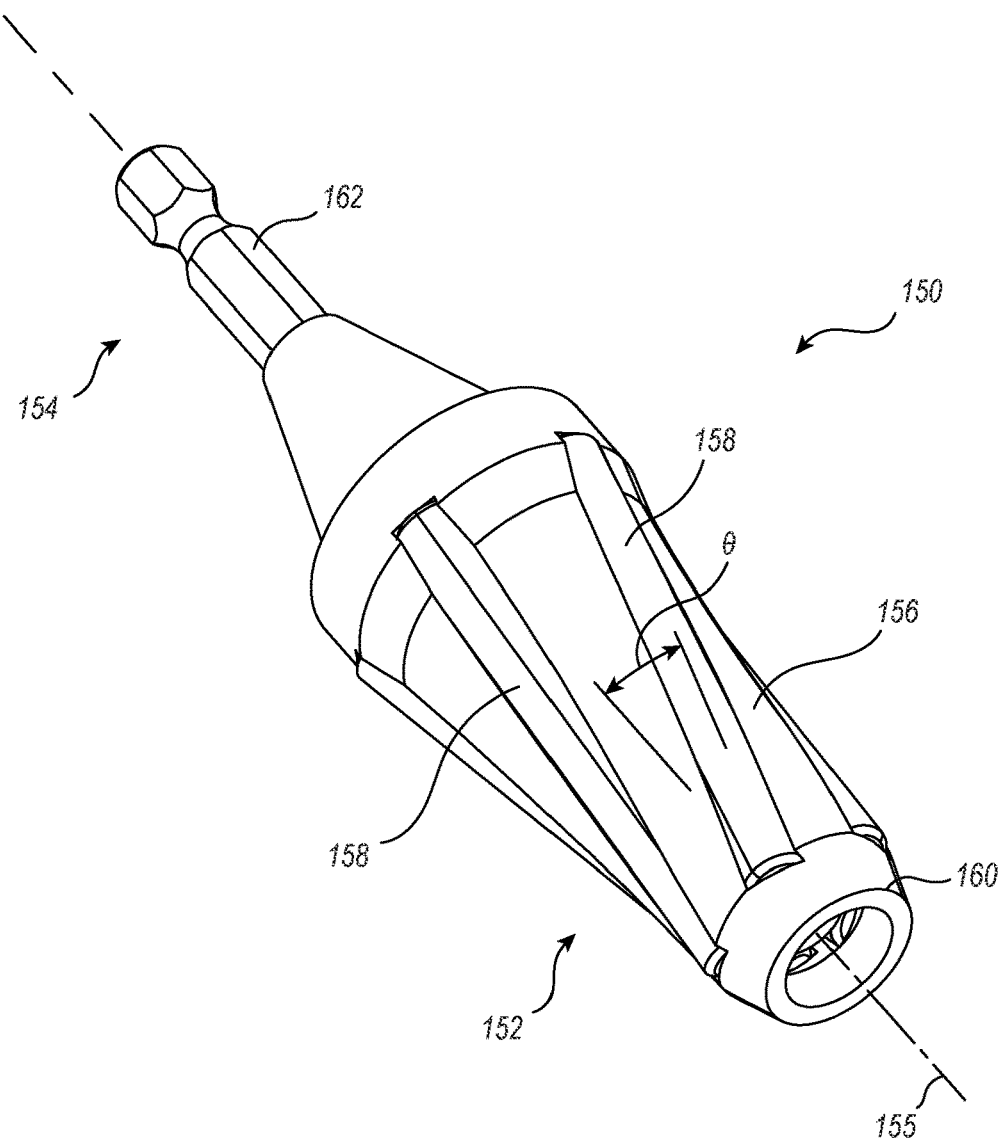
FIG. 39 is a perspective view of an alternative embodiment of an expander in the form of a mandrel.
Figure 40:
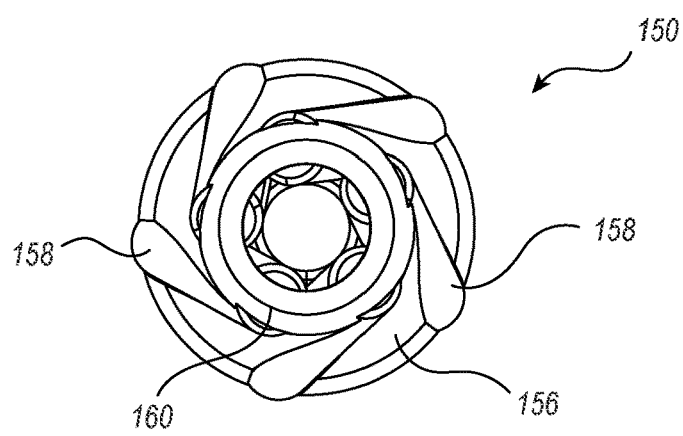
FIG. 40 is an elevated front view of the expander shown in FIG. 39.

It is also appreciated that the expander can come in a variety of different configurations. For example, depicted in FIGS. 39 and 40 is one alternative example of an expander 150, in the form of a mandrel, that can be used for expanding compression collars 10. Expander 150 has a first end 152 and an opposing second end 154 with a central longitudinal axis 155 extending through the opposing ends. Expander 150 includes an annular tapered body 156 that outwardly flares from first end 152 toward second end 154. A plurality of elongated, cylindrical rollers 158 are rotatably mounted on tapered body 156. Rollers 158 are radially spaced apart around tapered body 156 and extend along the length to tapered body 156 so that roller 158 also outwardly flare or project as they extend from first end 152 toward second end 154. Furthermore, rollers 150 are laterally sloped at an angle $\theta$ relative to central longitudinal axis 155. Angle $\theta$ is typically at least or less than 5°, 10°, 15°, 20°, 30°, 40° or in a range between any two of the foregoing. Other angles can also be used. Body 156 terminates at a tapered nose 160 at first end 152. Coupled with body 156 at second end 154 is a shank 162. Shank is configured to engage with a drill such as a hand drill or a drill press and typically has a cylindrical or polygonal transverse cross section.

During use, nose 160 is advanced into throughway 22 from one end of a compression collar 10. Compression collar 10 is held stationary while expander 150 is rotated. As rotating expander 150 is advanced into throughway 22, rollers 158 ride against and rotate over interior surface 14. Because of the outward projection or flare of rollers 158, rollers 158 radially outwardly expand compression collar 10 as expander 150 is pressed further into throughway 22. Furthermore, because rollers 158 are rolling over interior surface 14, rollers 158 produce low friction and do not damage compression collar 10. Expander 80 is advanced until compression collar 10 is sufficiently expanded to facilitate coupling with tube 40 and tube fitting 42, as previously discussed. If desired, separate expanders 150 can simultaneously advance into throughway 22 of compression collar 10 from the opposing ends for expansion. Likewise, expander 150 can be inserted consecutively into the opposing ends of compression collar 10 for expansion.

Figure 41:
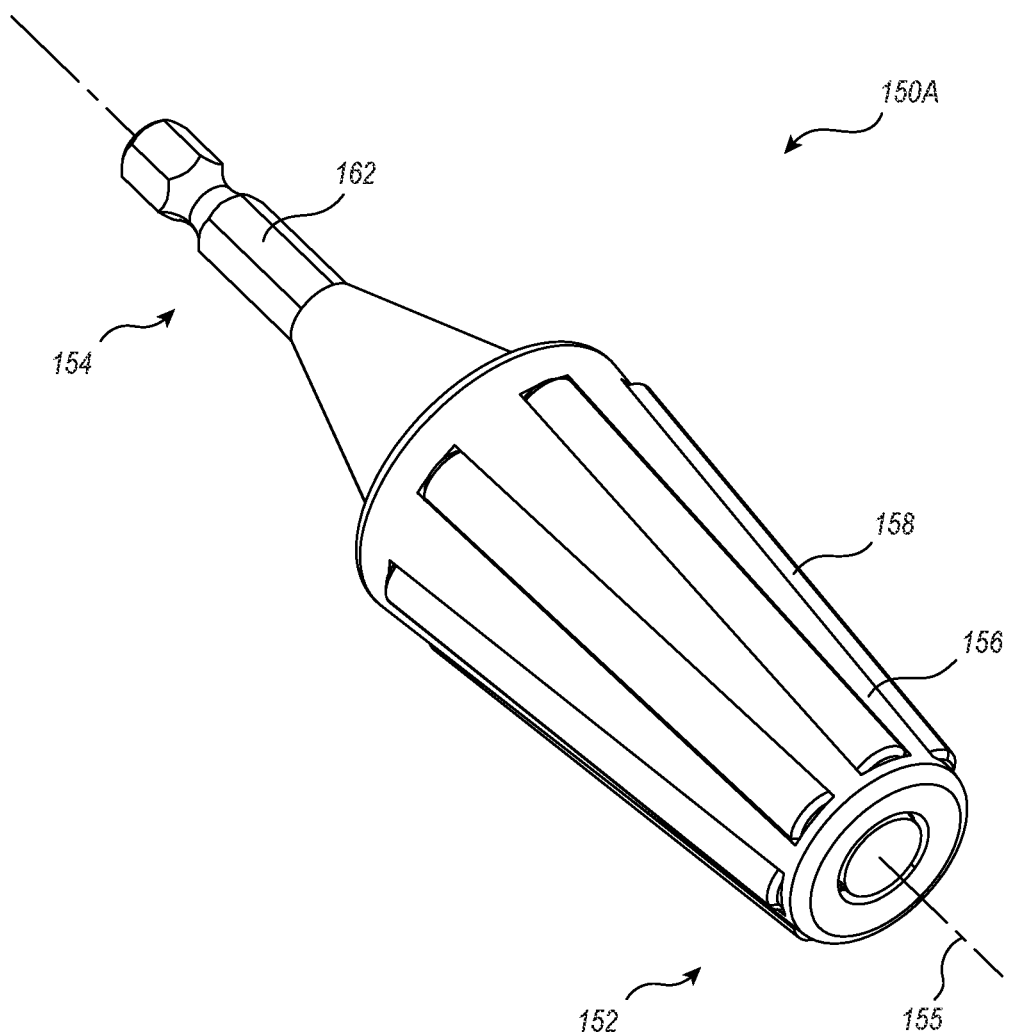
FIG. 41 is a perspective view of an alternative embodiment of the expander shown in FIG. 39 wherein the rollers are aligned with the longitudinal axis of the expander.

In contrast to laterally angling rollers 158 relative to longitudinal axis 155, as shown in FIG. 39, rollers 158 can also be aligned with longitudinal axis 155. For example, FIG. 41 shows an alternative expander 150A that is substantially identical to expander 150 except that rollers 150 are all aligned with longitudinal axis 155. Expander 150A can be used in the same way as expander 150 as discussed above.

Figure 42:
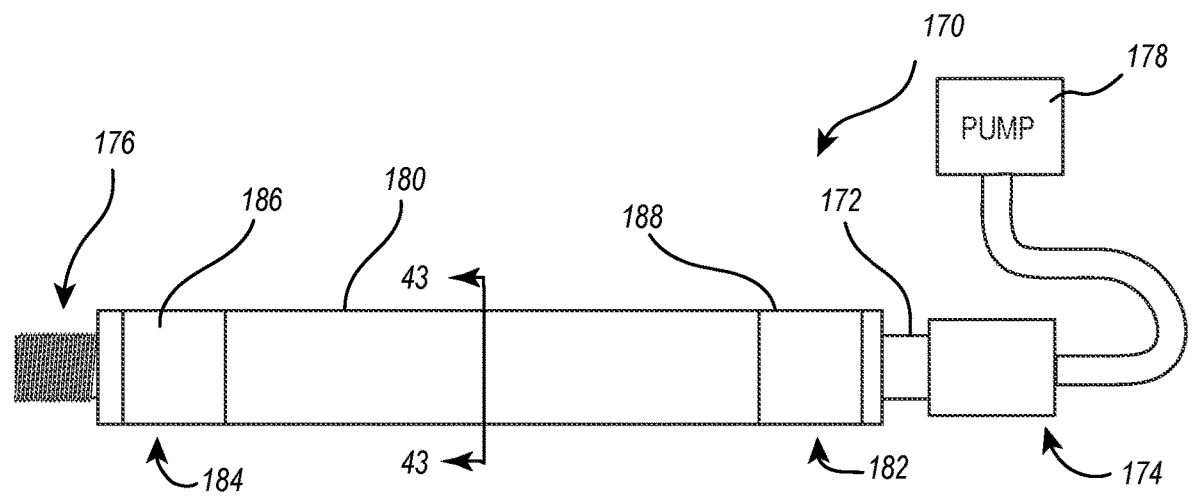
FIG. 42 is an elevated side view of an alternative expander having a bladder in an unexpanded state.
Figure 43:
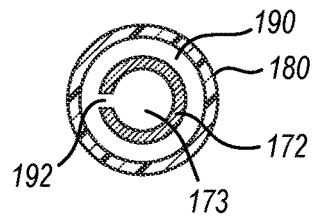
FIG. 43 is a cross sectional side view of the expander shown in FIG. 42 taken along lines 43-43.
Figure 44:
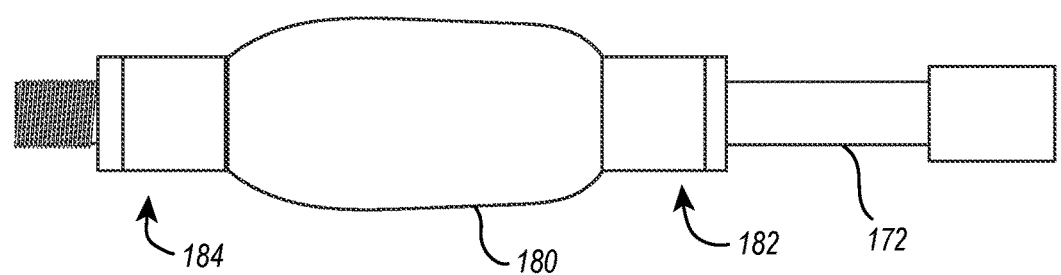
FIG. 44 is an elevated side view of the expander shown in FIG. 42 with the bladder in an expanded state.

Depicted in FIGS. 42-44 is a further alternative embodiment of an expander 170 that can be used to expand any of the compression collars disclosed herein. Expander 170 comprises an elongated tubular stem 172 having a channel 173 extending between a first end 174 and an opposing second end 176. Channel 173 is open at first end 174 but is sealed closed at second end 176. Stem 172 is typically made of a rigid material like a metal. A pump 178 is couple with first end 174 and is used to deliver hydraulic fluid into channel 173 of stem 172.

A tubular bladder 180 is disposed on and encircles stem 172. Bladder 180 has a first end 182 and an opposing second end 184. A clamp 186 securely fixes second end 184 of bladder 180 to second end 176 of stem 172 and forms a liquid tight seal therebetween. A clamp 188 is also disposed at first end 182 of bladder 180. Clamp 188, however, does not securely fix first end 182 of bladder 180 to stem 172. Rather, clamp 188 forms a liquid tight seal between first end 182 of bladder 180 and stem 172 but still permits first end 182 of bladder 180 to slide along stem 172. As needed, a gasket or other type of seal can be disposed between bladder 180 and stem 172 which assists in effecting the movable liquid tight seal. Bladder 180 is made of a resiliently expandable material.

A compartment 190 is formed between stem 172 and bladder 180 and is sealed closed on opposing ends by clamps 186 and 188. One or more openings 192 pass through stem 172 and provide fluid communication between channel 173 and compartment 190.

During use, a compression collar is slid over bladder 180 so as to encircle bladder between clamps 186 and 188. Hydraulic fluid is then pumped by pump 178 into channel 173 of stem 172. The hydraulic fluid passes through opening 192 and into compartment 190. As the pressure of the hydraulic fluid increases, bladder 180 radially outwardly expands causing the compression collar to expand from the contracted state to the expanded state. To accommodate for the expansion of bladder 180, first end 182 of bladder 180 slides toward second end 184 as bladder 180 expands. In this assembly, the central portion of bladder 180, which is encircled by the compression collar, expands in a substantially cylindrical configuration, thereby providing uniform expansion of the compression collar. Once the compression collar has moved to the expanded state, the pressure on the hydraulic fluid is released. Bladder 180 then resiliently retracts to its unexpanded state and the compression collar is removed for attachment. As a result of balder 180 being flexible, the use of bladder 180 limits damage to the compression collar as the compression collar is expanded to the expanded state.

The inventive compression collars achieve a number of unique benefits. For example, because of the design and manufacturing process, the compression collars have rounded corners and are void of sharps both prior to and after attachment to tube 40 and tube fitting 42. As such, the compression collars provide minimal risk of damage to adjacent structures, such as polymeric bag or tubes, even when folded together. As such, minimal or no special packaging may be required to be applied around the compression collars, thereby minimizing manufacturing time and cost.

Furthermore, in contrast to traditional cable ties, the compression collar provides a uniform and constant compressive force entirely around the tube fitting. As such, there is a less chance for leakage or contamination passing between tube 40 and tube fitting 42, even when tube 40 is being moved. In addition, the compression collars provide a secure engagement between tube 40 and tube fitting 42, thereby preventing any unwanted or accidental separation or leaking between tube 40 and tube fitting 42. This secure engagement can potentially be further enhanced by the application of radiation to the compression collars after the compression collars have resiliently rebounded from the expanded state. Furthermore, in contrast to cable ties, the compression collars are easy to attach and guarantee a more consistent compressive force that is less subject to errors produced by those assembling the systems. In part, this is because the inventive compression collars are wider than cable ties, thereby compressing tube over a longer length of tube fitting 42 which improves the sealed engagement. In addition, unlike cable ties which can relax their compressive force over time, the compression collars will maintain their compressive force over time. The compression collars can also provide a higher compressive force than cable ties. The windows 26, 146, spacer tabs 24, and/or stop lips 32 also provide unique advantages of both ensuring and being able to confirm that the coupled tube fitting 42 and tube 40 are properly positioned within the compression collars for proper compression and sealing therebetween. Other advantages also exist.

Although the compression collars depicted herein achieve functional benefits, they are also designed to have aesthetic attributes. For example, the compression collars are provide curved lines and symmetry that provide a unique aesthetic appeal to the compression collars.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for sealing a tube to a tube fitting, the method comprising:
    radially expanding a compression collar from a constricted state to an expanded state, wherein the compression collar is resiliently flexible, tubular and comprises a throughway extending through the compression collar;
    positioning the throughway of the compression collar over at least a portion of the tube and the tube fitting;
    allowing the compression collar to resiliently rebound to compress the tube against the tube fitting; and
    applying a first type of radiation to the compression collar while or after the compression collar resiliently rebounds to the constricted state to further seal the tube to the tube fitting and sterilize the compression collar and seal.

2. The method as recited in claim 1, wherein radially expanding the compression collar comprises radially expanding the compression collar prior to positioning the throughway of the compression collar over at least the portion of the tube and the tube fitting.

3. The method as recited in claim 1, wherein applying the first type of radiation to the compression collar comprises applying the first type of radiation to the compression collar prior to radially expanding the compression collar.

4. The method as recited in claim 1, further comprising applying the first type of radiation to the compression collar prior to positioning the throughway of the compression collar over at least a portion of the tube and the tube fitting.

5. The method as recited in claim 1, further comprising applying the first type of radiation to the tube and tube fitting to sterilize the tube and tube fitting.

6. The method as recited in claim 1, wherein the tubular compression collar is comprised of polyethylene.

7. The method as recited in claim 1, wherein the first type of radiation comprises gamma radiation.

8. The method as recited in claim 1, wherein applying the first type of radiation to the compression collar increases cross-linking of the compression collar.

9. The method as recited in claim 1, wherein applying the first type of radiation to the compression collar increases a compressive strength of the compression collar.

10. The method as recited in claim 1, wherein applying the first type of radiation to the compression collar comprises subjecting the compression collar to at least 50 kGy of gamma radiation.

11. The method as recited in claim 1, wherein applying the first type of radiation to the compression collar comprises subjecting the compression collar to at least 80 kGy of gamma radiation.

12. The method as recited in claim 7, wherein the gamma radiation increases a stiffness of the compression collar.

13. The method as recited in claim 1, wherein the compression collar is comprised of high-density polyethylene (HDPE).

14. The method as recited in claim 1, further comprising applying a second type of radiation to the compression collar.

15. The method as recited in claim 14, wherein the second type of radiation is an electron beam and applying an electron beam to the compression collar comprises applying an electron beam to the compression collar prior to applying the first type of radiation to the compression collar.

16. The method as recited in claim 14, wherein applying the second type of radiation to the compression collar comprises applying an electron beam to the compression collar prior to expanding the compression collar.

17. The method as recited in claim 14, wherein applying the second type of radiation to the compression collar comprises applying an electron beam to the compression collar prior to prior to positioning the throughway of the compression collar over at least a portion of the tube and the tube fitting.

18. The method as recited in claim 1, wherein the tube is in contact with a biological fluid.

19. The method as recited in claim 1, wherein the tube is connected to a biological processing container.

20. The method as recited in claim 1, wherein the compression collar comprises a diameter, and wherein radially expanding the compression collar comprises radially expanding the diameter of the compression collar by at least 50 percent of a diameter from an unexpanded state to the expanded state.

21. The method as recited in claim 20, wherein allowing the compression collar to resiliently rebound comprises allowing a diameter of the expanded compression collar to constrict by at least 50-90 percent of a diameter from the expanded state.

* * * * *